US006582706B1

(12) United States Patent
Johnson et al.

(10) Patent No.: US 6,582,706 B1
(45) Date of Patent: Jun. 24, 2003

(54) **VACCINE COMPOSITIONS COMPRISING *STREPTOCOCCUS PNEUMONIAE* POLYPEPTIDES HAVING SELECTED STRUCTURAL MOTIFS**

(75) Inventors: Leslie S. Johnson, Germantown, MD (US); John E. Adamou, Rockville, MD (US)

(73) Assignee: MedImmune, Inc., Gaithersburg, MD (US)

( * ) Notice: Subject to any disclaimer, the term of this patent is extended or adjusted under 35 U.S.C. 154(b) by 0 days.

(21) Appl. No.: 09/468,656

(22) Filed: Dec. 21, 1999

Related U.S. Application Data

(60) Provisional application No. 60/113,048, filed on Dec. 21, 1998.

(51) Int. Cl.[7] ................................................ A61K 39/09

(52) U.S. Cl. ................................ 424/244.1; 424/184.1; 424/185.1; 424/190.1; 424/237.1; 435/69.1; 435/320.1; 530/350; 536/23.1; 536/23.7

(58) Field of Search ........................... 424/184.1, 185.1, 424/190.1, 237.1, 244.1; 435/69.1, 320.1; 514/94; 530/350; 536/23.1, 23.7

(56) References Cited

U.S. PATENT DOCUMENTS 6,042,838 A * 3/2000 Briles et al. ............. 424/244.1

FOREIGN PATENT DOCUMENTS

| | | | |
|---|---|---|---|
| WO | WO 95/06732 | | 3/1995 |
| WO | WO 97/48417 | | 6/1996 |
| WO | WO 97/41151 | | 11/1997 |
| WO | WO-98/18930 | A2 * | 5/1998 |
| WO | WO 98/18930 | | 5/1998 |
| WO | WO 98/18931 | | 5/1998 |
| WO | WO 99/15675 | | 4/1999 |
| WO | WO 00/17370 | | 3/2000 |
| WO | WO 00/39299 | | 7/2000 |

OTHER PUBLICATIONS

Paul et al. Fundamental Immunology, Raven Press, New York, NY (1993) 3rd Edition, p. 251.*

Riffkin et al. A single amino–acid change between the antigenically different extracellular serine proteases V2 and B2 from Dichelobacter nodosus. Gene (1995) vol. 167, pp. 279–283.*

Abaza et al. Effects of amino acid substitutions outside an antigenic site on protein binding to monoclonal antibodies of predetermined specificity obtained by peptide immunization. Journal of Protein Chemistry (1992) vol. 11, No. 5, pp. 433–444.*

Paul W.E. In Fundamental Immunology (1993) Raves Press, New York, pp. 249–251.*

Ristori et al. Compositional bias and mimicry toward the non–self proteome in immunodominant T cell epeitpopes of self and nonself antigens. FASEB Journal (2000) vol. 14, pp. 431–438.*

Cundell, et al., "Receptor specificity of adherence of *Streptococcus pneumoniae* to human type–11 pneumocytes and vascular endothelial cells in vitro" *Micro. Path.* vol. 17, pp. 361–374 (1994).

Cundell et al., "*Streptococcus pneumoniae* anchor to activated human cells by the receptor for platelet–activating factor", *Nature*, vol. 377, pp. 435–438 (1995).

Tuomanen et al., "Alcohol Consumption and Mortality Among Women", *New Engl. J. Med.*, vol. 322, pp. 1280–1284 (1995).

Idanpaan–Heikkila et al., "Oligosaccharides Interfere with the Establishment and Progression of Experimental Pneumococcal Pneumonia", *J. Inf. Dis.*, vol. 176, pp. 704–712 (1997).

Lupas et al., "Predicting Coiled Coils from Protein Sequences", *Sciences*, vol. 252, pp. 1162–1164 (1991).

* cited by examiner

*Primary Examiner*—James Housel
*Assistant Examiner*—Ulrike Winkler
(74) *Attorney, Agent, or Firm*—Elliot M. Olstein; Alan J. Grant

(57) ABSTRACT

A vaccine composition is disclosed that comprises polypeptides and fragments of polypeptides containing histidine triad residues or coiled-coil regions, some of which polypeptides or fragments lie between 80 and 680 residues in length. Also disclosed are processes for preventing infection caused by *S. pneumoniae* comprising administering of vaccine compositions.

11 Claims, 32 Drawing Sheets

FIGURE 6A

```
      C S Y E L G R H Q A G Q X K K E S N R V S Y I D G D Q A G Q K A E N L T P D E V S K R E G I N A E Q   Majority
                          10                            20                            30                            40                            50
  1   C S Y E L G R H Q A G Q V K K E S N R V S Y I D G D Q A G Q K A E N L T P D E V S K R E G I N A E Q   PhtD. PRO
  1   C S Y E L G R Y Q A G Q D K K E S N R V A Y I D G D Q A G Q K A E N L T P D E V S K R E G I N A E Q   PhtB. PRO
  1   C S Y E L G L Y Q A - R T V K E N N R V S Y I D G K Q A T Q K T E N L T P D E V S K R E G I N A E Q   PhtA. PRO
  1   C A Y A L N Q H R S - Q E N K D N N R V S Y V D G S Q S S Q K S E N L T P D Q V S Q K E G I Q A E Q   PhtE. PRO

      I V I K I T D Q G Y V T S H G D H Y H Y Y N G K V P Y D A I I S E E L L M K D P N Y Q L K D S D I V   Majority
                          60                            70                            80                            90                           100
 51   I V I K I T D Q G Y V T S H G D H Y H Y Y N G K V P Y D A I I S E E L L M K D P N Y Q L K D S D I V   PhtD. PRO
 51   I V I K I T D Q G Y V T S H G D H Y H Y Y N G K V P Y D A I I S E E L L M K D P N Y Q L K D S D I V   PhtB. PRO
 50   I V I K I T D Q G Y V T S H G D H Y H Y Y N G K V P Y D A I I S E E L L M K D P N Y K L K D E D I V   PhtA. PRO
 50   I V I K I T D Q G Y V T S H G D H Y H Y Y N G K V P Y D A L F S E E L L M K D P N Y Q L K D A D I V   PhtE. PRO

      N E V K G G Y V I K V D G K Y Y V Y L K D A A H A D N V R T K E E I N R Q K Q E H S H N H E G G - -   Majority
                          110                           120                           130                           140                           150
101   N E I K G G Y V I K V D G K Y Y V Y L K D A A H A D N I R T K E E I K R Q K Q E H S H N H G G G - -   PhtD. PRO
101   N E I K G G Y V I K V N G K Y Y V Y L K D A A H A D N I R T K E E I K R Q K Q E R S H N H N S - - -   PhtB. PRO
100   N E V K G G Y V I K V D G K Y Y V Y L K D A A H A D N V R T K E E I N R Q K Q E H S Q H R E G G T P   PhtA. PRO
100   N E V K G G Y I I K V D G K Y Y V Y L K D A A H A D N V R T K D E I N R Q K Q E H V K D N E - - - -   PhtE. PRO
```

FIGURE 6B

```
     R N D X A V A A A R A Q G R Y T T D D G Y I F N A S D I I E D T G D A Y I V P H G D H Y H Y I P K N  Majority
                160                 170                 180                 190                 200
149  S N D Q A V V A A R A Q G R Y T T D D G Y I F N A S D I I E D T G D A Y I V P H G D H Y H Y I P K N  PhtD. PRO
148  R A D N A V A A A R A Q G R Y T T D D G Y I F N A S D I I E D T G D A Y I V P H G D H Y H Y I P K N  PhtB. PRO
150  R N D G A V A L A R S Q G R Y T T D D G Y I F N A S D I I E D T G D A Y I V P H G D H Y H Y I P K N  PhtA. PRO
146  K V N S N V A V A R S Q G R Y T T N D G Y V F N P A D I I E D T G N A Y I V P H G G H Y H Y I P K S  PhtE. PRO

     E L S A S E L A A A E A Y L N G K - - - - - - - - - - - Q G S R P S S S S S Y N A N P A Q P R L S E  Majority
                210                 220                 230                 240                 250
199  E L S A S E L A A A E A Y W N G K - - - - - - - - - - - Q G S R P S S S S S Y N A N P A Q P R L S E  PhtD. PRO
198  E L S A S E L A A A E A Y W N G K - - - - - - - - - - - Q G S R P S S S S S Y N A N P A Q P R L S E  PhtB. PRO
200  E L S A S E L A A A E A F L S G R G N L S N S R T Y R R Q N S D N T S R T N W V P S V S N P G T T N  PhtA. PRO
196  D L S A S E L A A A K A H L A G K - - - - - - - - - - - - - N M Q P S Q L S Y S S T A S D - - - N N  PhtE. PRO

     T H N L T V T P T Y H Q A N Q G E N I S S L L K E L Y A K P L S E R H V E S D G L V F D P A Q I T S  Majority
                260                 270                 280                 290                 300
238  N H N L T V T P T Y H Q - N Q G E N I S S L L R E L Y A K P L S E R H V E S D G L I F D P A Q I T S  PhtD. PRO
237  N H N L T V T P T Y H Q - N Q G E N I S S L L R E L Y A K P L S E R H V E S D G L I F D P A Q I T S  PhtB. PRO
250  T N T S N N S N T N S Q A S Q S N D I D S L L K Q L Y K L P L S Q R H V E S D G L V F D P A Q I T S  PhtA. PRO
230  T Q S V A K G S T S K P A N K S E N L Q S L L K E L Y D S P S A Q R Y S E S D G L V F D P A K I I S  PhtE. PRO
```

FIGURE 6C

```
    R T A R G V A V P H G D H Y H F I P Y S Q M S E L E E R I A R I I P L R Y R S N H W V P D S R P E Q  Majority
                        310                           320                           330                           340                           350
287 R T A R G V A V P H G N H Y H F I P Y E Q M S E L E K R I A R I I P L R Y R S N H W V P D S R P E Q  PhtD. PRO
286 R T A R G V A V P H G N H Y H F I P Y E Q M S E L E K R I A R I I P L R Y R S N H W V P D S R P E E  PhtB. PRO
300 R T A R G V A V P H G D H Y H F I P Y S Q M S E L E E R I A R I I P L R Y R S N H W V P D S R P E Q  PhtA. PRO
280 R T P N G V A I P H G D H Y H F I P Y S K L S A L E E K I A R M V P I - - - - - - - - - - - - - - -  PhtE. PRO

    P S P Q P T P E P S P S P Q P A P N - - - A P S N P I D X K L V K E A V R K V G D G Y V F E E N G V  Majority
                        360                           370                           380                           390                           400
337 P S P Q S T P E P S P S P Q P A P N P Q P A P S N P I D E K L V K E A V R K V G D G Y V F E E N G V  PhtD. PRO
336 P S P Q P T P E P S P S P Q P - - - - - - A P S N P I D G K L V K E A V R K V G D G Y V F E E N G V  PhtB. PRO
350 P S P Q P T P E P S P G P Q P A P N L K I D S - - - - N S S L V S Q L V R K V G E G Y V F E E K G I  PhtA. PRO
315 - - - - - - - - - - - - - - - - - - - - - - - - - - - - - - - - - - - - - - - - - - - - - - - S G T  PhtE. PRO

    S R Y V P A K D L S A E T A A G L D S K L A K Q E S L S H K L G A K K T D L P S S D R E F Y N K A Y  Majority
                        410                           420                           430                           440                           450
387 S R Y I P A K D L S A E T A A G I D S K L A K Q E S L S H K L G A K K T D L P S S D R E F Y N K A Y  PhtD. PRO
380 S R Y I P A K D L S A E T A A G I D S K L A K Q E S L S H K L G T K K T D L P S S D R E F Y N K A Y  PhtB. PRO
396 S R Y V F A K D L P S E T V K N L E S K L S K Q E S V S H T L T A K K E N V A P R D Q E F Y D K A Y  PhtA. PRO
318 G S T V S T N A K P N E V V S S L G S - - - - - - - - - - - L S S N P S S L T T S - - - - - - - - -  PhtE. PRO
```

FIGURE 6D

```
     D L L A R I H Q D L L D N K G R Q V D F E A L D N L L E R L K D V S S D K V K L V D D I L A F L A P  Majority
                 460                 470                 480                 490                 500
437  D L L A R I H Q D L L D N K G R Q V D F E A L D N L L E R L K D V P S D K V K L V D D I L A F L A P  PhtD. PRO
430  D L L A R I H Q D L L D N K G R Q V D F E A L D N L L E R L K D V S S D K V K L V E D I L A F L A P  PhtB. PRO
448  N L L T E A H K A L F E N K G R N S D F Q A L D K L L E R L N D E S T N K E K L V D D L L A F L A P  PhtA. PRO
348  - - - - - - - - - - - - - - - - - - - - - - - - - - - - - - K E L S S - - - - - - - - - - - - - - -  PhtE. PRO

     I R H P E R L G K P N A Q I T Y T D D E I Q V A K L A G K Y T A S D G Y I F D P R D I T S D E G D A  Majority
                 510                 520                 530                 540                 550
487  I R H P E R L G K P N A Q I T Y T D D E I Q V A K L A G K Y T T E D G Y I F D P R D I T S D E G D A  PhtD. PRO
480  I R H P E R L G K P N A Q I T Y T D D E I Q V A K L A G K Y T A E D G Y I F D P R D I T S D E G D A  PhtB. PRO
496  I T H P E R L G K P N S Q I E Y T E D E V R I A Q L A D K Y T T S D G Y I F D E H D I I S D E G D A  PhtA. PRO
353  - - - - - - - - - - - - - - - - - - - - - - - - - - - - - - - A S D G Y I F N P K D I V E E T A T A  PhtE. PRO

     Y V T P H M T H S H W I K K D S L S E A E R A A A Q A Y A K E K G L T P P S T D H Q D S G N T E A K  Majority
                 560                 570                 580                 590                 600
537  Y V T P H M T H S H W I K K D S L S E A E R A A A Q A Y A K E K G L T P P S T D H Q D S G N T E A K  PhtD.PRO
530  Y V T P H M T H S H W I K K D S L S E A E R A A A Q A Y A X E K G L T P P S T D H Q D S G N T E A K  PhtB.pro
546  Y V T P H M G H S H W I G K D S L S D K E K V A A Q A Y T K E K G I L P P S P D A D V K A N P T G D  PhtA.PRO
372  Y I V R H G D H F H Y I P K - - - - - - S N Q I G Q P T L P N N S L A T P S P S L P I N P G T S H E K  PhtE.PRO
```

FIGURE 6E

```
    G A E A I Y N R V K A A K K V P L D R M P Y N L Q Y T V E V K N G S L I I P H Y D H Y H N I K F E W  Majority
                      610                           620                           630                           640                           650
587 G A E A I Y N R V K A A K K V P L D R M P Y N L Q Y T V E V K N G S L I I P H Y D H Y H N I K F E W  PhtD.PRO
580 G A E A I Y N R V K A A K K V P L D R M P Y N L Q Y T V E V K N G S L I I P H Y D H Y H N I K F E W  PhtB.pro
596 S A A A I Y N R V K G E K R I P L V R L P Y M V E H T V E V K N G N L I I P H K D H Y M N I K F A W  PhtA.PRO
417 H E E D G Y G - - - - - - - - - - - - - - F D A N R I I A E D E S G F V M S H G D H N H - - - - - -  PhtE.PRO

    F D E G L Y E A P K G Y T L E D L L A T V K Y Y V E H P N E R P H S D N G F G N A S D H V X X N K X  Majority
                      660                           670                           680                           690                           700
637 F D E G L Y E A P K G Y T L E D L L A T V K Y Y V E H P N E R P H S D N G F G N A S D H V R K N K V  PhtD.PRO
630 F D E G L Y E A P K G Y T L E D L L A T V K Y Y V E H P N E R P H S D N G F G N A S D H V Q R N K N  PhtB.pro
646 F D D H T Y K A P N G Y T L E D L F A T I K Y Y V E H P D E R P H S N D G W G N A S E H V L G K K D  PhtA.PRO
447 - - - - - - - - - - - - - - - - - - - - - - Y F - - - - - - - - - - - - - - - - - - - - - - - - - -  PhtE.PRO

    X Q X D X N X X X K X X E E X - - - - - - - P E - - - - - - - - - - - P - - - - - - - - - - - - - -  Majority
                      710                           720                           730                           740                           750
687 D Q D S K P D E D K E H D E V S E P T H P E S D E K E N H A G L N P S A D N L Y K P S T D T E E T E  PhtD. PRO
680 G Q A D T N Q T E K P S E E K P Q T E K P E E E T - - - - - - - - P R E E K P Q S E K P E S P K P T  PhtB. PRO
696 H S E D P N K N F K A D E E P - - - - - - - - - - - - - - - - - - - - - - - - - - - - - - - - - - -  PhtA. PRO
449 - - - - - - - - - - - - - - - - - - - - - - - - - - - - - - - - - - - - - - - - - - - - - - - - - -  PhtE. PRO
```

FIGURE 6F

```
     E E X E E T P X E X E X P Q V E T E K V E A K L Z E A E X L L X K V T D P S I K X N A X E T L T G L   Majority
                       760                           770                           780                           790                           800
737  E E A E D T T D E A E I P Q V E N S V I N A K I A D A E A L L E K V T D P S I R Q N A M E T L T G L   PhtD. PRO
722  E E P E E S P E E S E E P Q V E T E K V E E K L R E A E D L L G K I Q D P I I K S N A K E T L T G L   PhtB. PRO
711  - - V E E T P A E P E V P Q V E T E K V E A Q L K E A E V L L A K V T D S S L K A N A T E T L A G L   PhtA. PRO
449  - - - - - - - - - - - - - - - - - - - F K K D L T E E Q I - - - - - - - - - - - - - - - - - - - - -   PhtE. PRO

     K N N L L L G T X D N N T I M A E A E K L L A L L K E S X P X X X - - - K - - K - -   Majority
                       810                           820                           830                           840
787  K S S L L L G T K D N N T I S A E V D S L L A L L K E S Q P A P I   PhtD. PRO
772  K N N L L F G T Q D N N T I M A E A E K L L A L L K E S K   PhtB. PRO
759  R N N L T L Q I M D N N S I M A E A E K L L A L L K G S N P S S V S K E K I N K L N   PhtA. PRO
459  - - - - - - - - - - - - - - - - - - - - - - - - - - - - - - - - - - - - K V R K N I   PhtE. PRO
```

FIGURE 7A

| | | |
|---|---|---|
| | TCCTATGAGCTTGGA-GTTATCAAGCTGGTCAGGTTAAGAAAGAGTCTAA | Majority |
| | 10 20 30 40 50 | |
| 61 | TCTTACGAGTTGGGACTGTATCAAGCTAGAACGGTTAAGGAAAA---TAA | phtA.SEQ |
| 1 | TCCTATGAGCTTGGACGTTACCAAGCTGGTCAGGATAAGAAAGAGTCTAA | phtB.seq |
| 1 | TCCTATGAACTTGGTCGTCACCAAGCTGGTCAGGTTAAGAAAGAGTCTAA | phtD.SEQ |
| 64 | GCCTATGCACTAAACCAGCATC--GTTCG-CAGGAAAATAAGGACAATAA | phtE.SEQ |

| | | |
|---|---|---|
| | TCGTGTTTCTTATATAGATGGTGATCAGGCTGGTCAAAAGGCAGAAAACT | Majority |
| | 60 70 80 90 100 | |
| 108 | TCGTGTTTCCTATATAGATGGAAAACAAGCGACGCAAAAAACGGAGAATT | phtA.SEQ |
| 51 | TCGAGTTGCTTATATAGATGGTGATCAGGVTGGTCAAAAGGCAGAAAACT | phtB.seq |
| 51 | TCGAGTTTCTTATATAGATGGTGATCAGGCTGGTCAAAAGGCAGAAAACT | phtD.SEQ |
| 111 | TCGTGTCTCTTATGTGGATGGCAGCCAGTCAAGTCAGAAAAGTGAAAACT | phtE.SEQ |

| | | |
|---|---|---|
| | TGACACCAGATGAGGTTAGTAAGAGGGAGGGGATCAACGCTGAGCAAATT | Majority |
| | 110 120 130 140 150 | |
| 158 | TGACTCCTGATGAGGTTAGCAAGCGTGAAGGAATCAATGCTGAGCAAATC | phtA.SEQ |
| 101 | TGACACCAGATGAAGTCAGTAAGAGGGAGGGGATCAACGCCGAACAAATT | phtB.seq |
| 101 | TGACACCAGATGAAGTCAGTAAGAGGGAGGGGATCAACGCCGAACAAATC | phtD.seq |
| 161 | TGACACCAGACCAGGTTAGCCAGAAAGAAGGAATTCAGGCTGAGCAAATT | phtE SEQ |

FIGURE 7B

```
     GTCATCAAGATTACGGATCAAGGTTATGTGACCTCTCATGGAGACCATTA  Majority

               160       170       180       190       200

208  GTCATCAAGATAACAGACCAAGGCTATGTCACTTCACATGGCGACCACTA  phtA.SEQ
151  GTTATCAAGATTACGGATCAAGGTTATGTGACCTCTCATGGAGACCATTA  phtB.seq
151  GTCATCAAGATTACGGATCAAGGTTATGTGACCTCTCATGGAGACCATTA  phtD.SEQ
211  GTAATCAAAATTACAGATCAGGGCTATGTAACGTCACACGGTGACCACTA  phtE.SEQ

     TCATTACTATAATGGCAAGGTTCCTTATGATGCCATCATCAGTGAAGAGC  Majority

               210       220       230       240       250

258  TCATTATTACAATGGTAAGGTTCCTTATGACGCTATCATCAGTGAAGAAT  phtA.SEQ
201  TCATTACTATAATGGCAAGGTTCCTTATGATGCCATCATCAGTGAAGAGC  phtB.seq
201  TCATTACTATAATGGCAAGGTCCCTTATGATGCCATCATCAGTGAAGAGC  phtD.SEQ
261  TCATTACTATAATGGGAAAGTTCCTTATGATGCCCTCTTTAGTGAAGAAC  phtE.SEQ

     TCCTCATGAAACATCCGAATTATCAGTTGAAGGATTCAGATATTGTCAAT  Majority

               260       270       280       290       300

308  TACTCATGAAAGATCCAAACTATAAGCTAAAAGATGAGGATATTGTTAAT  phtA.SEQ
251  TCCTCATGAAAGATCCGAATTATCAGTTGAAGGATTCAGACATTGTCAAT  phtB.seq
251  TCCTCATGAAAGATCCGAATTATCAGTTGAAGGATTCAGACATTGTCAAT  phtD.SEQ
311  TCTTGATGAAGGATCCAAACTATCAACTTAAAGACGCTGATATTGTCAAT  phtE.SEQ
```

FIGURE 7C

```
     GAAGTCAAGGGTGGTTATGTTATCAAGGTAGATGGAAAATACTATGTTTA  Majority
                310       320       330       340       350

358  GAGGTCAAGGGTGGATATGTTATCAAGGTAGATGGAAAATACTATGTTTA  phtA.SEQ
301  GAAATCAAGGGTGGTTATGTCATTAAGGTAAACGGTAAATACTATGTTTA  phtB.seq
301  GAAATCAAGGGTGGTTATGTTATCAAGGTAGATGGAAAATACTATGTTTA  phtD.SEQ
361  GAAGTCAAGGGTGGTTATATCATCAAGGTCGATGGAAAATATTATGTCTA  phtE.SEQ

     CCTTAAGGATGCAGCTCATGCGGATAATGTTCGGACAAAAGAAGAGATTA  Majority
                360       370       380       390       400

408  CCTTAAGGATGCTGCCCACGCGGATAACGTCCGTACAAAAGAGGAAATCA  phtA.SEQ
351  CCTTAAGGATGCRGCTCATGCGGATAATATTCGGACAAAAGAAGAGATTA  phtB.seq
351  CCTTAAGGATGCAGCTCATGCGGATAATATTCGGACAAAAGAAGAGATTA  phtD.SEQ
411  CCTGAAAGATGCAGCTCATGCTGATAATGTTCGAACTAAAGATGAAATCA  phtE.SEQ

     ATCGTCAGAAGCAGGAACATAGTCATAATCATGAGGGTGGAXCT-----N  Majority
                410       420       430       440       450

458  ATCGACAAAAAGAAGAGCATAGTCAACATCGTGAAGGTGGAACTCCAAGA  phtA.SEQ
401  AACGTCAGAAGCAGGAACGCAGTCATAATCATAACTCAAGAGCA------  phtB.seq
401  AACGTCAGAAGCAGGAACACAGTCATAATCACGGGGGYGGYYCT------  phtD.SEQ
461  ATCGTCAAAAACAAGAACATGTCAAAGATAATGAG------------AAG  phtE.SEQ
```

FIGURE 7D

```
     GATGATXXTGCTGTTGCTGTAGCCAGATCCCAAGGACGCTATACAACGGA  Majority

               460       470       480       490       500

508  AACGATGGTGCTGTTGCCTTGGCACGTTCGCAAGGACGCTATACTACAGA  phtA.SEQ
445  GATAAT---GCTGTTGCTGCAGCCAGAGCCCAAGGACGTTATACAACGGA  phtB.seq
445  AACGATCAAGCAGTAGTTGCAGCCAGAGCCCAAGGACGCTATACAACGGA  phtD.SEQ
499  GTTAACTCTAATGTTGCTGTAGCAAGGTCTCAGGGACGATATACGACAAA  phtE.SEQ

     TGATGGTTATATCTTTAATGCATCTGATATCATTGAGGATACGGGTGATG  Majority

               510       520       530       540       550

558  TGATGGTTATATCTTTAATGCTTCTGATATCATAGAGGATACTGGTGATG  phtA.SEQ
492  TGATGGGTATATCTTCAATGCATCTGATATCATTGAGGACACGGGTGATG  phtB.seq
495  TGATGGTTATATCTTCAATGCATCTGATATCATTGAGGACACGGGTGATG  phtD.SEQ
549  TGATGGTTATGTCTTTAATCCAGCTGATATTATCGAAGATACGGGTAATG  phtE.SEQ

     CTTATATCGTTCCTCATGGCGATCATTACCATTACATTCCTAAGAATGAG  Majority

               560       570       580       590       600

608  CTTATATCGTTCCTCATGGAGATCATTACCATTACATTCCTAAGAATGAG  phtA.SEQ
542  CTTATATCGTTCCTCACGGCGACCATTACCATTACATTCCTAAGAATGAG  phtB.seq
545  CTTATATCGTTCCTCACGGCGACCATTACCATTACATTCCTAAGAATGAG  phtD.SEQ
599  CTTATATCGTTCCTCATGGAGGTCACTATCACTACATTCCCAAAAGCGAT  phtE.SEQ
```

FIGURE 7E

```
     TTATCAGCTAGCGAGTTAGCTGCTGCAGAAGCC----TATTTGGATGGGA  Majority
               610       620       630       640       650
658  TTATCAGCTAGCGAGTTGGCTGCTGCAGAAGCCTTCCTATCTGGTCGAGG  phtA.SEQ
592  TTATCAGCTAGCGAGTTAGCTGCTGCAGAAGCC----TATTGGAATGGGA  phtB.seq
595  TTATCAGCTAGCGAGTTAGCTGCTGCAGAAGCC----TATTGGAATGGGA  phtD.SEQ
649  TTATCTGCTAGTGAATTAGCAGCAGCTAAAGCAC----ATCTGGCTGGAA  phtE.SEQ

     AG------CAAAT--GGGATCTCGTCCTTCTTCAAGTTCTAGTTATACTT  Majority
               660       670       680       690       700
708  AAATCTGTCAAATTCAAGAACCTATCGCCGACAAAATAGCGATAACACTT  phtA.SEQ
638  AG------CA-----GGGATCTCGTCCTTCTTCAAGTTCTAGTTATAATG  phtB.seq
641  AG------CA-----GGGATCTCGTCCTTCTTCAAGTTCTAGTTATAATG  phtD.SEQ
695  A--------AAATATGCAACCGAGTC--------AGTTA-AGCTATTCTT  phtE.SEQ

     CAA-ATCCAGCTCAGTACCA-----AGATTGTCAGAGAACCACAAT--CT  Majority
               710       720       730       740       750
758  CAAGAACAAACTGGGTACCTTCTGTAAGCAATCCAGGAACTACAAATACT  phtA.SEQ
677  CAA-ATCCAGCTCA--ACCA-----AGATTGTCAGAGAACCACAAT--CT  phtB.seq
680  CAA-ATCCAGCTCA--ACCA-----AGATTGTCAGAGAACCACAAT--CT  phtD.SEQ
728  CAA----CAGCT-AGT----------GACAAT--AACA--CGCAATCTGT  phtE.SEQ
```

FIGURE 7F

```
     GACA-AAGCTGTCACTCCAACATTATCA-TCAAGCAAATCAAGGTGAAAA  majority

            760       770       780       790       800

808  AACACAAGCAACAACAGCAACACTAACAGTCAAGCAAGTCAAAGTAATGA  phtA.SEQ
717  GA------CTGTCACTCCAAC-TTATCA-TCAA---AATCAAGGGGAAAA  phtB.seq
720  GA------CTGTCACTCCAAC-TTATCA-TCAA---AATCAAGGGGAAAA  phtD.SEQ
759  AGCAAAAG-GATCA-------ACTAGCAAGCCAGCAAATAAATCTGAAAA  phtE.SEQ

     CATTTCAAGTCTTTTGCGTGAATTGTATGCTAAACCTTTATCAGAACGCC  Majority

            810       820       830       840       850

858  CATTGATAGTCTCTTGAAACAGCTCTACAAACTGCCTTTGAGTCAACGAC  phtA.SEQ
756  CATTTCAAGCCTTTTACGTGAATTGTATGCTAAACCCTTATCAGAACGCC  phtB.seq
759  CATTTCAAGCCTTTTACGTGAATTGTATCGTAAACCCTTATCAGAACGCC  phtD.SEQ
801  TCTCCAGAGTCTTTTGAAGGAACTCTATGATTCACCTAGCGCCCAACGTT  phtE.SEQ

     ATGTGGAATCTGATGGCCTTGTTTTTGACCCAGCGCAAATCACAAGTCGA  Majority

            860       870       880       890       900

908  ATGTAGAATCTGATGGCCTTGTCTTTGATCCAGCACAAATCACAAGTCGA  phtA.SEQ
806  ATGTGGAATCTGATGGCCTTATTTTCGACCCAGCGCAAATCACAAGTCGA  phtB.seq
809  ATGTGGAATCTGATGGCCTTATTTTCGACCCAGCGCAAATCACAAGTCGA  phtD.SEQ
851  ACAGTGAATCAGATGGCCTGGTCTTTGACCCTGCTAAGATTATCAGTCGT  phtE.SEQ
```

FIGURE 7G

```
     ACCGCCAGAGGTGTTGCTGTCCCTCATGGTGACCATTACCACTTTATCCC  Majority

               910       920       930       940       950

958  ACAGCTAGAGGTGTTGCAGTGCCACACGGAGATCATTACCACTTCATCCC  phtA.SEQ
856  ACCGCCAGAGGTGTAGCTGTCCCTCATGGTAACCATTACCACTTTATCCC  phtB.seq
859  ACCGCCAGAGGTGTAGCTGTCCCTCATGGTAACCATTACCACTTTATCCC  phtD.SEQ
901  ACACCAAATGGAGTTGCGATTCCGCATGGCGACCATTACCACTTTATTCC  phtE.SEQ

     TTATGAACAAATGTCTGAATTGGAAGAACGAATTGCTCGTATTATTCCCC  Majority

               960       970       980       990      1000

1008 TTACTCTCAAATGTCTGAATTGGAAGAACGAATCGCTCGTATTATTCCCC  phtA.SEQ
906  TTATGAACAAATGTCTGAATTGGAAAAACGAATTGCTCGTATTATTCCCC  phtB.seq
909  TTATGAACAAATGTCTGAATTGGAAAAACGAATTGCTCGTATTATTCCCC  phtD.SEQ
951  TTACAGCAAGCTTTCTGCCTTAGAAGAAAAGATTGCCAGAAT--------  phtE.SEQ

     TTCGTTATCGTTCAAACCATTGGGTACCAGATTCAAGACCAGAAGAACCA  majority

              1010      1020      1030      1040      1050

1058 TTCGTTATCGTTCAAACCATTGGGTACCAGATTCAAGGCCAGAACAACCA  phtA.SEQ
956  TTCGTTATCGTTCAAACCATTGGGTACCAGATTCAAGACCAGAAGAACCA  phtB.seq
959  TTCGTTATCGTTCAAACCATTGGGTACCAGATTCAAGACCAGAAGAACCA  phtD.SEQ
993  ----------------------GGTGCC----T----ATCAGTGGAACTG  phtE.SEQ
```

FIGURE 7H

```
     AGTCCACAATCGACTCCGGAACCTAGTCCAAGTCCGCAACCTGCACCAAA  Majority
               1060      1070      1080      1090      1100
1108 AGTCCACAACCGACTCCGGAACCTAGTCCAGGCCCGCAACCTGCACCAAA  phtA.SEQ
1006 AGTCCACAACCGACTCCAGAACCTAGTCCAAGTCCGCAACC---------  phtB.seq
1009 AGTCCACAATCGACTCCGGAACCTAGTCCAAGTCCGCAACCTGCACCAAA  phtD.SEQ
1013 GTTCTACAGTT----------TCTA---CAAA---------TGCA--AAA  phtE.SEQ

     TC-T-AA--AGCTCCAAGCAATCCAATTGATG-GAAATTGGTCAAAGAAG  Majority
               1110      1120      1130      1140      1150
1158 TCTTAAAATAGACTCAA---ATTCTTCT---------TTGGTTAGTCAGC  phtA.SEQ
1047 ---------AGCTCCAAGCAATCCAATTGATGGAAATTGGTCAAAGAAG  phtB.seq
1059 TCCTCAACCAGCTCCAAGCAATCCAATTGATGAGAAATTGGTCAAAGAAG  phtD.SEQ
1039 CC-------------------------TAATG------------------  phtE.SEQ

     CTGTTCGAAAAGTAGGCGATGGTTATGTCTTTGAGGAGAATGGAGTTTCT  Majority
               1160      1170      1180      1190      1200
1196 TGGTACGAAAAGTTGGGGAAGGATATGTATTCGAAGAAAAGGGCATCTCT  phtA.SEQ
1088 CTGTTCGAAAAGTAGGCGATGGTTATGTCTTTGAGGAGAATGGAGTTTCT  phtB.seq
1109 CTGTTCGAAAAGTAGGCGATGGTTATGTCTTTGAGGAGAATGGAGTTTCT  phtD.SEQ
1046 ---------AAGTAG----------TGTCT-------------AGTCT--  phte.SEQ
```

FIGURE 7I

```
      CGTTATATCCCAGCCAAGGATCTTTCAGCAGAAACAGCAGCAGGCATTGA  Majority

                1210      1220      1230      1240      1250

1246  CGTTATGTCTTTGCGAAAGATTTACCATCTGAAACTGTTAAAAATCTTGA  phtA.SEQ
1138  CGTTATATCCCAGCCAAGGATCTTTCAGCAGAAACAGCAGCAGGCATTGA  phtB.seq
1159  CGTTATATCCCAGCCAAGGATCTTTCAGCAGAAACAGCAGCAGGCATTGA  phtD.SEQ
1062  -----------------------------------------AGGC-----  phtE.SEQ

      TAGCAAACTGGCCAAGCAGGAAAGTTTTTCTCATAAGCTAGGAGCTAAGA  Majority

                1260      1270      1280      1290      1300

1296  AAGCAAGTTATCAAAACAAGAGACTGTTTCACACACTTTAACTGCTAAAA  phtA.SEQ
1188  TAGCAAACTGGCCAAGCAGGAAAGTTTATCTCATAAGCTAGGAACTAAGA  phtB.seq
1209  TAGCAAACTGGCCAAGCAGGAAAGTTTATCTCATAAGCTAGGAGCTAAGA  phtD.SEQ
1074  -AAGCAATCCTTCTTCT-------------TTAACGACAAG---------  phtE.SEQ

      AAACTGATCTTCCTTCTAGTGATCGAGAATTTTACGATAAGGCTTATGAC  Majority

                1310      1320      1330      1340      1350

1346  AAGAAAATGTTGCTCCTCGTGACCAAGAATTTTATGATAAAGCATATAAT  phtA.SEQ
1238  AAACTGACCTCCCATCTAGTGATCGAGAATTTTACAATAAGGCTTATGAC  phtB.seq
1259  AAACTGACCTCCCATCTAGTGATCGAGAATTTTACAATAAGGCTTATGAC  phtD.SEQ
1074  -AAGCAATCCTTCTTCT-------------TTAACGACAAG---------  phtE.SEQ
```

FIGURE 7J

```
      TTACTAGCAAGAATTCACCAAGATTTACTTGATAATAAGGGTCGACAAGT  Majority

                1360      1370      1380      1390      1400

1396  CTGTTAACTGAGGCTCATAAAGCCTTGTTTGNAAATAAGGGTCGTAATTC  phtA.SEQ
1288  TTACTAGCAAGAATTCACCAAGATTTACTTGATAATAAAGGTCGACAAGT  phtB.seq
1309  TTACTAGCAAGAATTCACCAAGATTTACTTGATAATAAAGGTCGACAAGT  phtD.SEQ
1101  -----------------------------------TAAGGA---------  phtE.SEQ

      TGATTTTGAGGCTTAGGATAACCTGTTGGAACGACTCAAGGATGTCTCAA  Majority

                1410      1420      1430      1440      1450

1446  TGATTTCCAAGCCTTAGACAAATTATTAGAACGCTTGAATGATGAATCGA  phtA.SEQ
1338  TGATTTTGAGGCTTTGGATAACCTGTTGGAACGACTCAAGGATGTCTCAA  phtB.seq
1359  TGATTTTGAGGCTTTGGATAACCTGTTGGAACGACTCAAGGATGTCCCAA  phtD.SEQ
1107  --------------------------------------------------  phtE.SEQ

      GTGATAAAGTCAAGTTAGTGGATGATATTCTTGCCTTCTTAGCTCCGATT  Majority

                1460      1470      1480      1490      1500

1496  CTAATAAAGAAAAATTGGTAGATGATTTATTGGCATTCCTAGCACCAATT  phtA.SEQ
1388  GTGATAAAGTCAAGTTAGTGGAAGATATTCTTGCCTTCTTAGCTCCGATT  phtB.seq
1409  GTGATAAAGTCAAGTTAGTGGATGATATTCTTGCCTTCTTAGCTCCGATT  phtD.SEQ
1107  --------------------------------GCTCTCTT----------  phtE.SEQ
```

FIGURE 7K

```
      CGTCATCCAGAACGTTTAGGAAAACCAAATGCGCAAATTACCTACACTGA  Majority

                1510      1520      1530      1540      1550

1546  ACCCATCCAGAGCGACTTGGCAAACCAAATTCTCAAATTGAGTATACTGA  phtA.SEQ
1438  CGTCATCCAGAACGTTTAGGAAAACCAAATGCGCAAATTACCTACACTGA  phtB.seq
1459  CGTCATCCAGAACGTTTAGGAAAACCAAATGCGCAAATTACCTACACTGA  phtD.SEQ
1115  --------------------------------------------------  phtE.SEQ

      TGATGAGATTCAAGTAGCCAAGTTGGCAGGCAAGTACACAGCATCAGATG  Majority

                1560      1570      1580      1590      1600

1596  AGACGAACTTCGTATTGCTCAATTAGCTGATAAGTATACAACGTCAGATG  phtA.SEQ
1488  TGATGAGATTCAAGTAGCCAAGTTGGCAGGCAAGTACACAGCAGAAGACG  phtB.seq
1509  TGATGAGATTCAAGTAGCCAAGTTGGCAGGCAAGTACACAACAGAAGACG  phtD.SEQ
1115  --------------------------------------CAGCATCTGATG  phtE.SEQ

      GTTATATTTTTGATCCTCGTGATATAACCAGTGATGAGGGGGATGCCTAT  Majority

                1610      1620      1630      1640      1650

1646  GTTACATTTTTGATGAACATGATATAATCAGTGATGAAGGAGATGCATAT  phtA.SEQ
1538  GTTATATCTTTGATCCTCGTGATATAACCAGTGATGAGGGGGATGCCTAT  phtB.seq
1559  GTTATATCTTTGATCCTCGTGATATAACCAGTGATGAGGGGGATGCCTAT  phtD.SEQ
1127  GTTATATTTTTAATCC----------------------------------  phtE.SEQ
```

FIGURE 7L

```
     GTAACTCCACATATGACCCATAGCCACTGGATTAAAAAAGATAGTTTGTC  Majority

               1660      1670      1680      1690      1700

1696 GTAACGCCTCATATGGGCCATAGTCACTGGATTGGAAAAGATAGCCTTTC  phtA.SEQ
1588 GTAACTCCACATATGACCCATAGCCACTGGATTAAAAAAGATAGTTTGTC  phtB.seq
1609 GTAACTCCACATATGACCCATAGCCACTGGATTAAAAAAGATAGTTTGTC  phtD.SEQ
1143 -----------------------------------AAAAGATA-----TC  phtE.SEQ

     TGAAGCTGAGAGAGCGGCAGCCCAGGCTTATGCTAAAGAGAAAGGTTTGA  Majority

               1710      1720      1730      1740      1750

1746 TGATAAGGAAAAAGTTGCAGCTCAAGCCTATACTAAAGAAAAAGGTATCC  phtA.SEQ
1638 TGAAGCTGAGAGAGCGGCAGCCCAGGCTTATGCTAAAGAGAAAGGTTTGA  phtB.seq
1659 TGAAGCTGAGAGAGCGGCAGCCCAGGCTTATGCTAAAGAGAAAGGTTTGA  phtD.SEQ
1153 ----GTTGAAGAAACGGC--------------------------------  phtE.SEQ

     CCCCTCCTTCGACAGACCATCAGGATTCAGGAAATACTGAGGCAAAAGGA  Majority

               1760      1770      1780      1790      1800

1796 TACCTCCATCTCCAGACGCAGATGTTAAAGCAAATCCAACTGGAGATAGT  phtA.SEQ
1688 CCCCTCCTTCGACAGACCATCAGGATTCAGGAAATACTGAGGCAAAAGGA  phtB.seq
1709 CCCCTCCTTCGACAGACCATCAGGATTCAGGAAATACTGAGGCAAAAGGA  phtD.SEQ
1167 --------------------------------------------------  phtE.SEQ
```

FIGURE 7M

```
       GCAGAAGCTATCTACAACCGXGTGAAAGCAGCTAAGAAGGTGCCACTTGA  Majority
                 1810      1820      1830      1840      1850
1846   GCAGCAGCTATTTACAATCGTGTGAAAGGGGAAAAAGCAATTCCACTCGT  phtA.SEQ
1738   GCAGAAGCTATCTACAACCGXGTGAAAGCAGCTAAGAAGGTGCCACTTGA  phtB.seq
1759   GCAGAAGCTATCTACAACCGXGTGAAAGCAGCTAAGAAGGTGCCACTTGA  phtD.SEQ
1167   ------------TACAGCT-------------------------------  phtE.SEQ

       TCGTATGCCTTACAATCTTCAATATACTGTAGAAGTCAAAAACGGTAGTT  Majority
                 1860      1870      1880      1890      1900
1896   TCGACTTCCATATATGGTTGAGCATACAGTTGAGGTTAAAAACGGTAATT  phtA.SEQ
1788   TCGTATGCCTTACAATCTTCAATATACTGTAGAAGTCAAAAACGGTAGTT  phtB.seq
1809   TCGTATGCCTTACAATCTTCAATATACTGTAGAAGTCAAAAACGGTAGTT  phtD.SEQ
1174   ----------------------TATATTGTAAGA----------------  phtE.SEQ

       TAATCATACCTCATTATGATCATTACCATAACATTAAATTTGAGTGGTTT  Majority
                 1910      1920      1930      1940      1950
1946   TGATTATTCCTCATAAGGATCATTACCATAATATTAAATTTGCTTGGTTT  phtA.SEQ
1838   TAATCATACCTCATTATGATCATTACCATAACATTAAATTTGAGTGGTTT  phtB.seq
1859   TAATCATACCTCATTATGATCATTACCATAACATTAAATTTGAGTGGTTT  phtD.SEQ
1186   -----------CATGGTGATCATTTCCATTACATT---------------  phtE.SEQ
```

FIGURE 7N

```
       GACGAAGGCCTTTATGAGGCACCTAAGGGGTATACTCTTGAGGATCTTTT  Majority

                1960      1970      1980      1990      2000

1996   GATGATCACACATACAAAGCTCCAAATGGCTATACCTTGGAAGATTTGTT  phtA.SEQ
1888   GACGAAGGCCTTTATGAGGCACCTAAGGGGTATACTCTTGAGGATCTTTT  phtB.seq
1909   GACGAAGGCCTTTATGAGGCACCTAAGGGGTATACTCTTGAGGATCTTTT  phtD.SEQ
1210   ----------------------CCAAA-----------------------  phtE.SEQ

       GGCGACTGTCAAGTACTATGTCGAACATCCAGACGAACGTCCGCATTCAG  Majority

                2010      2020      2030      2040      2050

2046   TGCGACGATTAAGTACTACGTAGAACACCCTGACGAACGTCCACATTCTA  phtA.SEQ
1938   GGCGACTGTCAAGTACTATGTCGAACATCCAGACGAACGTCCGCATTCAG  phtB.seq
1959   GGCGACTGTCAAGTACTATGTCGAACATCCAGACGAACGTCCGCATTCAG  phtD.SEQ
1215   -------ATCAAT--CAAATTGGGCAACC-GAC------TCT---TCCAA  phtE.SEQ

       ATAATGGTTTTGGTAACGCTAGCGACCATGTTTTXA-AAACAAGAAAGAT  Majority

                2060      2070      2080      2090      2100

2096   ATGATGGATGGGGCAATGCCAGTGAGCATGTGTT---AGGCAAGAAAGAC  phtA.SEQ
1988   ATAATGGTTTTGGTAACGCTAGCGACCATGTTCAAAGAAACAAAAATGGT  phtB.seq
2009   ATAATGGTTTTGGTAACGCTAGCGACCATGTTCGTAAAAATAAGGTAGAC  phtD.SEQ
1247   ACAATAG-TCTAGCAACACCTTCT-CCATCTCTTC-----CAA------T  phtE.SEQ
```

FIGURE 7O

```
      CAAGCCAGTAAACCTAATGAAGATGAGAAACATGACCAAGTAAG-GAG--  Majority

                2110      2120      2130      2140      2150

2143  CA------------CAGTGAAGAT-----------CCAAATAAG------  phtA.SEQ
2038  CAAGCTGATA---CCAATCAA-ACGGAAAA----ACCAAGCGAG-GAGAA  phtB.seq
2059  CAAGACAGTAAACCTGATGAAGATAAGGAACATGATGAAGTAAGTGAGCC  phtD.SEQ
1284  CAATCCAG-GAACTTCAC----ATGAGAAACATGA---------------  phtE.SEQ

      A-CTCA--C-GAA-----TGAAGAAGA-AACCACG--G-TTTAAATCCT-  Majority

                2160      2170      2180      2190      2200

2164  ----------------------------AAC--------TTCAAA-----  phtA.SEQ
2079  ACCTCAGACAGAAAAACCTGAGGAAGA-AACC--------------CCTC  phtB.seq
2109  AACTCACCCTGAATCTGATGAAAAAGAGAATCACGCTGGTTTAAATCCTT  phtD.SEQ
1314  ---------------------AGAAGATGGATACG--GATTTGA-TGCT-  phtE.SEQ

      -AGCAGATAAACCGTATAAGCCAG--AC-----------A-AC--A---A  Majority

                2210      2220      2230      2240      2250

2173  --GCGGATGAA------GAGCCAG--------------------------  phtA.SEQ
2114  GAGAAGAGAAACCGCA-AAGCGAGAAACCAGAGTCTCCAAAACCAACAGA  phtB.seq
2159  CAGCAGATAATCTTTATAAACCAAGCACTGATACGGAAGAGACAGAGGAA  phtD.SEQ
1339  ------AATCGTATTATC--------------------------------  phtE.SEQ
```

FIGURE 7P

```
      G-AGCTGGAGGAAXCACCAGATGAGTCAGAAGTXCCTCAAGTAGAGACTG  Majority
                2260      2270      2280      2290      2300
2189  -----TAGAGGAAACACCTGCTGAGCCAGAAGTCCCTCAAGTAGAGACTG  phtA.SEQ
2163  GGAACCAGAAGAATCACCAGAGGAATCAGAAGAACCTCAGGTCGAGACTG  phtB.seq
2209  GAAGCTGAAGATACCAC-AGATGAGGCTGAAATTCCTCAAGTAGAGAATT  phtD.SEQ
1351  ---GCTGAAGA----------TGAATC-----------------------  phtE.SEQ

      AAAAXGTTGAAGCXAAACTXAXAGAXGCXGAGGTTTTGCTTGXAAAAGTC  Majority
                2310      2320      2330      2340      2350
2234  AAAAAGTAGAAGCCCAACTCAAAGAAGCAGAAGTTTTGCTTGCGAAAGTA  phtA.SEQ
2213  AAAAGGTTGAAGAAAAACTGAGAGAGGCTGAAGATTTACTTGGAAAAATC  phtB.seq
2258  CTGTTATTAACGCTAAGATAGCAGATGCGGAGGCCTTGCTAGAAAAAGTA  phtD.SEQ
1365  ------------------------------AGGTTTTG----------TC  phtE.SEQ

      ACGGATCCTAGTATXAAAXCCAATGCXACGGAGACTCTXACTGGTTTAAA  Majority
                2360      2370      2380      2390      2400
2284  ACGGATTCTAGTCTGAAAGCCAATGCAACAGAAACTCTAGCTGGTTTACG  phtA.SEQ
2263  CAGGATCCAATTATCAAGTCCAATGCCAAAGAGACTCTCACAGGATTAAA  phtB.seq
2308  ACAGATCCTAGTATTAGACAAAATGCTATGGAGACATTGACTGGTCTAAA  phtD.SEQ
1375  ATGAGTC--------------------ACGGAGACC--------------  phtE.SEQ
```

FIGURE 7Q

```
      AAATAATTTXCTTCTTGGAACXAAGGATAATAATACTATTTTGGCAGAAG  Majority

                2410      2420      2430      2440      2450

2334  AAATAATTTGACTCTTCAAATTATGGATAACAATAGTATCATGGCAGAAG  phtA.SEQ
2313  AAATAATTTACTATTTGGCACCCAGGACAACAATACTATTATGGCAGAAG  phtB.seq
2358  AAGTAGTCTTCTTCTCGGAACGAAAGATAATAACACTATTTCAGCAGAAG  phtD.SEQ
1391  --------------------------ACAAT--CATTATTTCTTCA----  phtE.SEQ

      CAGAAAGACTATTGGCTTTGTTAAAGGAGAGTAAXT-AAGGT-----CTT  Majority

                2460      2470      2480      2490      2500

2384  CAGAAAAATTACTTGCGTTGTTAAAACCAAGTAATC-----------CTT  phtA.SEQ
2363  CTGAAAAACTATTGGCTTTATTAAAGGAGAGTAAGTAAAGGTAGAAGCTT  phtB.seq
2408  TAGATAGTCTCTTGGCTTTGTTAAAAGAAAGT-----------------C  phtD.SEQ
1409  -AGAAGGACT--TGAC--------AGAAGAGCAAATTAAGGT--------  phtE.SEQ

      AA--GCG--TCTGGC-CCTA-G-CAA-AA-A-T--TATGGXAAAAGCTXA  Majority

                2510      2520      2530      2540      2550

2423  CA-------TCTG-----TAAG-------------TAAGGAAAAAT----  phtA.SEQ
2413  AAGGGCGAATTTGGCACCCAGGACAACAATACTATTATGGCAGAAGCTGA  phtB.seq
2441  AA--------CCGGCTCCTA---------------TATAGTAAAAGCTTA  phtD.SEQ
1440  ----GCG----------------CAAAAACATT----TAG            phtE.SEQ
```

FIGURE 7R

| | | |
|---|---|---|
| | AAAACTAXX | Majority |
| 2445 | | phtA.SEQ |
| 2463 | AAAACTATT | phtB.seq |
| 2468 | AG------CC | phtD.SEQ |
| 1455 | | phtE.SEQ |

Strain SJ2 (serotype 6B)

Strain EF6796 (serotype 6A)

Strain EF5668 (serotype 4)

SEQUENCE LISTING

```
<160> NUMBER OF SEQ ID NOS: 14

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Forward
      primer used in amplification of the Sp36 gene sequence.

<400> SEQUENCE: 1

atcggatcct tcttacgagt tgggactgta tcaagc                              36


<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Forward
      primer used in amplification of the Sp36 gene sequence.

<400> SEQUENCE: 2

atcggatcca ctgtatcaag ctagaacggt taagg                               35


<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Reverse
      primer used in amplification of the Sp36 gene sequence.

<400> SEQUENCE: 3

agtcaagctt gtttattttt tccttactta cagatgaagg                          40


<210> SEQ ID NO 4
<211> LENGTH: 838
<212> TYPE: PRT
<213> ORGANISM: Streptococcus pneumoniae

<400> SEQUENCE: 4

Met Lys Ile Asn Lys Lys Tyr Leu Ala Gly Ser Val Ala Val Leu Ala
  1               5                  10                  15

Leu Ser Val Cys Ser Tyr Glu Leu Gly Arg His Gln Ala Gly Gln Val
             20                  25                  30

Lys Lys Glu Ser Asn Arg Val Ser Tyr Ile Asp Gly Asp Gln Ala Gly
         35                  40                  45

Gln Lys Ala Glu Asn Leu Thr Pro Asp Glu Val Ser Lys Arg Glu Gly
     50                  55                  60

Ile Asn Ala Glu Gln Ile Val Ile Lys Ile Thr Asp Gln Gly Tyr Val
 65                  70                  75                  80

Thr Ser His Gly Asp His Tyr His Tyr Tyr Asn Gly Lys Val Pro Tyr
                 85                  90                  95

Asp Ala Ile Ile Ser Glu Glu Leu Leu Met Lys Asp Pro Asn Tyr Gln
            100                 105                 110

Leu Lys Asp Ser Asp Ile Val Asn Glu Ile Lys Gly Gly Tyr Val Ile
        115                 120                 125

Lys Val Asp Gly Lys Tyr Tyr Val Tyr Leu Lys Asp Ala Ala His Ala
    130                 135                 140

Asp Asn Ile Arg Thr Lys Glu Glu Ile Lys Arg Gln Lys Gln Glu His
```

-continued

```
145                 150                 155                 160

Ser His Asn His Gly Gly Gly Ser Asn Asp Gln Ala Val Val Ala Ala
                165                 170                 175

Arg Ala Gln Gly Arg Tyr Thr Thr Asp Asp Gly Tyr Ile Phe Asn Ala
            180                 185                 190

Ser Asp Ile Ile Glu Asp Thr Gly Asp Ala Tyr Ile Val Pro His Gly
        195                 200                 205

Asp His Tyr His Tyr Ile Pro Lys Asn Glu Leu Ser Ala Ser Glu Leu
    210                 215                 220

Ala Ala Ala Glu Ala Tyr Trp Asn Gly Lys Gln Gly Ser Arg Pro Ser
225                 230                 235                 240

Ser Ser Ser Ser Tyr Asn Ala Asn Pro Ala Gln Pro Arg Leu Ser Glu
                245                 250                 255

Asn His Asn Leu Thr Val Thr Pro Thr Tyr His Gln Asn Gln Gly Glu
            260                 265                 270

Asn Ile Ser Ser Leu Leu Arg Glu Leu Tyr Ala Lys Pro Leu Ser Glu
        275                 280                 285

Arg His Val Glu Ser Asp Gly Leu Ile Phe Asp Pro Ala Gln Ile Thr
    290                 295                 300

Ser Arg Thr Ala Arg Gly Val Ala Val Pro His Gly Asn His Tyr His
305                 310                 315                 320

Phe Ile Pro Tyr Glu Gln Met Ser Glu Leu Glu Lys Arg Ile Ala Arg
                325                 330                 335

Ile Ile Pro Leu Arg Tyr Arg Ser Asn His Trp Val Pro Asp Ser Arg
            340                 345                 350

Pro Glu Gln Pro Ser Pro Gln Ser Thr Pro Glu Pro Ser Pro Ser Pro
        355                 360                 365

Gln Pro Ala Pro Asn Pro Gln Pro Ala Pro Ser Asn Pro Ile Asp Glu
    370                 375                 380

Lys Leu Val Lys Glu Ala Val Arg Lys Val Gly Asp Gly Tyr Val Phe
385                 390                 395                 400

Glu Glu Asn Gly Val Ser Arg Tyr Ile Pro Ala Lys Asp Leu Ser Ala
                405                 410                 415

Glu Thr Ala Ala Gly Ile Asp Ser Lys Leu Ala Lys Gln Glu Ser Leu
            420                 425                 430

Ser His Lys Leu Gly Ala Lys Lys Thr Asp Leu Pro Ser Ser Asp Arg
        435                 440                 445

Glu Phe Tyr Asn Lys Ala Tyr Asp Leu Leu Ala Arg Ile His Gln Asp
    450                 455                 460

Leu Leu Asp Asn Lys Gly Arg Gln Val Asp Phe Glu Ala Leu Asp Asn
465                 470                 475                 480

Leu Leu Glu Arg Leu Lys Asp Val Pro Ser Asp Lys Val Lys Leu Val
                485                 490                 495

Asp Asp Ile Leu Ala Phe Leu Ala Pro Ile Arg His Pro Glu Arg Leu
            500                 505                 510

Gly Lys Pro Asn Ala Gln Ile Thr Tyr Thr Asp Asp Glu Ile Gln Val
        515                 520                 525

Ala Lys Leu Ala Gly Lys Tyr Thr Thr Glu Asp Gly Tyr Ile Phe Asp
    530                 535                 540

Pro Arg Asp Ile Thr Ser Asp Glu Gly Asp Ala Tyr Val Thr Pro His
545                 550                 555                 560

Met Thr His Ser His Trp Ile Lys Lys Asp Ser Leu Ser Glu Ala Glu
                565                 570                 575
```

-continued

```
Arg Ala Ala Ala Gln Ala Tyr Ala Lys Glu Lys Gly Leu Thr Pro Pro
            580                 585                 590

Ser Thr Asp His Gln Asp Ser Gly Asn Thr Glu Ala Lys Gly Ala Glu
        595                 600                 605

Ala Ile Tyr Asn Arg Val Lys Ala Ala Lys Lys Val Pro Leu Asp Arg
    610                 615                 620

Met Pro Tyr Asn Leu Gln Tyr Thr Val Glu Val Lys Asn Gly Ser Leu
625                 630                 635                 640

Ile Ile Pro His Tyr Asp His Tyr His Asn Ile Lys Phe Glu Trp Phe
                645                 650                 655

Asp Glu Gly Leu Tyr Glu Ala Pro Lys Gly Tyr Thr Leu Glu Asp Leu
            660                 665                 670

Leu Ala Thr Val Lys Tyr Tyr Val Glu His Pro Asn Glu Arg Pro His
        675                 680                 685

Ser Asp Asn Gly Phe Gly Asn Ala Ser Asp His Val Arg Lys Asn Lys
    690                 695                 700

Val Asp Gln Asp Ser Lys Pro Asp Glu Asp Lys Glu His Asp Glu Val
705                 710                 715                 720

Ser Glu Pro Thr His Pro Glu Ser Asp Glu Lys Glu Asn His Ala Gly
                725                 730                 735

Leu Asn Pro Ser Ala Asp Asn Leu Tyr Lys Pro Ser Thr Asp Thr Glu
            740                 745                 750

Glu Thr Glu Glu Glu Ala Glu Asp Thr Thr Asp Glu Ala Glu Ile Pro
        755                 760                 765

Gln Val Glu Asn Ser Val Ile Asn Ala Lys Ile Ala Asp Ala Glu Ala
    770                 775                 780

Leu Leu Glu Lys Val Thr Asp Pro Ser Ile Arg Gln Asn Ala Met Glu
785                 790                 795                 800

Thr Leu Thr Gly Leu Lys Ser Ser Leu Leu Leu Gly Thr Lys Asp Asn
                805                 810                 815

Asn Thr Ile Ser Ala Glu Val Asp Ser Leu Leu Ala Leu Leu Lys Glu
            820                 825                 830

Ser Gln Pro Ala Pro Ile
        835
```

<210> SEQ ID NO 5
<211> LENGTH: 2531
<212> TYPE: DNA
<213> ORGANISM: Streptococcus pneumoniae

<400> SEQUENCE: 5

```
atgaaaatta ataaaaaata tctagcaggt tcagtggcag tccttgccct aagtgtttgt     60

tcctatgaac ttggtcgtca ccaagctggt caggttaaga aagagtctaa tcgagtttct    120

tatatagatg gtgatcaggc tggtcaaaag gcagaaaact tgacaccaga tgaagtcagt    180

aagagggagg ggatcaacgc cgaacaaatc gtcatcaaga ttacggatca aggttatgtg    240

acctctcatg gagaccatta tcattactat aatggcaagg tcccttatga tgccatcatc    300

agtgaagagc tcctcatgaa agatccgaat tatcagttga aggattcaga cattgtcaat    360

gaaatcaagg gtggttatgt tatcaaggta gatggaaaat actatgttta ccttaaggat    420

gcagctcatg cggataatat tcggacaaaa gaagagatta aacgtcagaa gcaggaacac    480

agtcataatc acgggggtgg ttctaacgat caagcagtag ttgcagccag agcccaagga    540

cgctatacaa cggatgatgg ttatatcttc aatgcatctg atatcattga ggacacgggt    600
```

-continued

```
gatgcttata tcgttcctca cggcgaccat taccattaca ttcctaagaa tgagttatca    660
gctagcgagt tagctgctgc agaagcctat tggaatggga agcagggatc tcgtccttct    720
tcaagttcta gttataatgc aaatccagct caaccaagat tgtcagagaa ccacaatctg    780
actgtcactc caacttatca tcaaaatcaa ggggaaaaca tttcaagcct tttacgtgaa    840
ttgtatgcta aacccttatc agaacgccat gtggaatctg atggccttat tttcgaccca    900
gcgcaaatca caagtcgaac cgccagaggt gtagctgtcc ctcatggtaa ccattaccac    960
tttatccctt atgaacaaat gtctgaattg gaaaaacgaa ttgctcgtat tattcccctt   1020
cgttatcgtt caaaccattg ggtaccagat tcaagaccag aacaaccaag tccacaatcg   1080
actccggaac ctagtccaag tccgcaacct gcaccaaatc ctcaaccagc tccaagcaat   1140
ccaattgatg agaaattggt caaagaagct gttcgaaaag taggcgatgg ttatgtcttt   1200
gaggagaatg gagtttctcg ttatatccca gccaaggatc tttcagcaga aacagcagca   1260
ggcattgata gcaaactggc caagcaggaa agtttatctc ataagctagg agctaagaaa   1320
actgacctcc catctagtga tcgagaattt tacaataagg cttatgactt actagcaaga   1380
attcaccaag atttacttga taataaaggt cgacaagttg attttgaggc tttggataac   1440
ctgttggaac gactcaagga tgtcccaagt gataaagtca agttagtgga tgatattctt   1500
gccttcttag ctccgattcg tcatccagaa cgtttaggaa aaccaaatgc gcaaattacc   1560
tacactgatg atgagattca agtagccaag ttggcaggca agtacacaac agaagacggt   1620
tatatctttg atcctcgtga tataaccagt gatgaggggg atgcctatgt aactccacat   1680
atgacccata gccactggat taaaaaagat agtttgtctg aagctgagag agcggcagcc   1740
caggcttatg ctaaagagaa aggtttgacc cctccttcga cagaccatca ggattcagga   1800
aatactgagg caaaaggagc agaagctatc tacaaccgcg tgaaagcagc taagaaggtg   1860
ccacttgatc gtatgcctta caatcttcaa tatactgtag aagtcaaaaa cggtagttta   1920
atcatacctc attatgacca ttaccataac atcaaatttg agtggtttga cgaaggcctt   1980
tatgaggcac ctaaggggta tactcttgag gatcttttgg cgactgtcaa gtactatgtc   2040
gaacatccaa acgaacgtcc gcattcagat aatggttttg gtaacgctag cgaccatgtt   2100
cgtaaaaata aggtagacca agacagtaaa cctgatgaag ataaggaaca tgatgaagta   2160
agtgagccaa ctcaccctga atctgatgaa aaagagaatc acgctggttt aaatccttca   2220
gcagataatc tttataaacc aagcactgat acggaagaga cagaggaaga agctgaagat   2280
accacagatg aggctgaaat tcctcaagta gagaattctg ttattaacgc taagatagca   2340
gatgcggagg ccttgctaga aaaagtaaca gatcctagta ttagacaaaa tgctatggag   2400
acattgactg gtctaaaaag tagtcttctt ctcggaacga aagataataa cactatttca   2460
gcagaagtag atagtctctt ggctttgtta aaagaaagtc aaccggctcc tatatagtaa   2520
aagcttaagc c                                                        2531
```

<210> SEQ ID NO 6
<211> LENGTH: 484
<212> TYPE: PRT
<213> ORGANISM: Streptococcus pneumoniae

<400> SEQUENCE: 6

```
Met Lys Phe Ser Lys Lys Tyr Ile Ala Ala Gly Ser Ala Val Ile Val
  1               5                  10                  15

Ser Leu Ser Leu Cys Ala Tyr Ala Leu Asn Gln His Arg Ser Gln Glu
```

-continued

```
            20                  25                  30

Asn Lys Asp Asn Asn Arg Val Ser Tyr Val Asp Gly Ser Gln Ser Ser
        35                  40                  45

Gln Lys Ser Glu Asn Leu Thr Pro Asp Gln Val Ser Gln Lys Glu Gly
    50                  55                  60

Ile Gln Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Leu Phe Ser Glu Glu Leu Leu Met Lys Asp Pro Asn Tyr Gln
            100                 105                 110

Leu Lys Asp Ala Asp Ile Val Asn Glu Val Lys Gly Gly Tyr Ile Ile
        115                 120                 125

Lys Val Asp Gly Lys Tyr Tyr Val Tyr Leu Lys Asp Ala Ala His Ala
    130                 135                 140

Asp Asn Val Arg Thr Lys Asp Glu Ile Asn Arg Gln Lys Gln Glu His
145                 150                 155                 160

Val Lys Asp Asn Glu Lys Val Asn Ser Asn Val Ala Val Ala Arg Ser
                165                 170                 175

Gln Gly Arg Tyr Thr Thr Asn Asp Gly Tyr Val Phe Asn Pro Ala Asp
            180                 185                 190

Ile Ile Glu Asp Thr Gly Asn Ala Tyr Ile Val Pro His Gly Gly His
        195                 200                 205

Tyr His Tyr Ile Pro Lys Ser Asp Leu Ser Ala Ser Glu Leu Ala Ala
    210                 215                 220

Ala Lys Ala His Leu Ala Gly Lys Asn Met Gln Pro Ser Gln Leu Ser
225                 230                 235                 240

Tyr Ser Ser Thr Ala Ser Asp Asn Asn Thr Gln Ser Val Ala Lys Gly
                245                 250                 255

Ser Thr Ser Lys Pro Ala Asn Lys Ser Glu Asn Leu Gln Ser Leu Leu
            260                 265                 270

Lys Glu Leu Tyr Asp Ser Pro Ser Ala Gln Arg Tyr Ser Glu Ser Asp
        275                 280                 285

Gly Leu Val Phe Asp Pro Ala Lys Ile Ile Ser Arg Thr Pro Asn Gly
    290                 295                 300

Val Ala Ile Pro His Gly Asp His Tyr His Phe Ile Pro Tyr Ser Lys
305                 310                 315                 320

Leu Ser Ala Leu Glu Glu Lys Ile Ala Arg Met Val Pro Ile Ser Gly
                325                 330                 335

Thr Gly Ser Thr Val Ser Thr Asn Ala Lys Pro Asn Glu Val Val Ser
            340                 345                 350

Ser Leu Gly Ser Leu Ser Ser Asn Pro Ser Ser Leu Thr Thr Ser Lys
        355                 360                 365

Glu Leu Ser Ser Ala Ser Asp Gly Tyr Ile Phe Asn Pro Lys Asp Ile
    370                 375                 380

Val Glu Glu Thr Ala Thr Ala Tyr Ile Val Arg His Gly Asp His Phe
385                 390                 395                 400

His Tyr Ile Pro Lys Ser Asn Gln Ile Gly Gln Pro Thr Leu Pro Asn
                405                 410                 415

Asn Ser Leu Ala Thr Pro Ser Pro Ser Leu Pro Ile Asn Pro Gly Thr
            420                 425                 430

Ser His Glu Lys His Glu Glu Asp Gly Tyr Gly Phe Asp Ala Asn Arg
        435                 440                 445
```

-continued

Ile Ile Ala Glu Asp Glu Ser Gly Phe Val Met Ser His Gly Asp His
    450                 455                 460

Asn His Tyr Phe Phe Lys Lys Asp Leu Thr Glu Glu Gln Ile Lys Val
465                 470                 475                 480

Arg Lys Asn Ile

<210> SEQ ID NO 7
<211> LENGTH: 1455
<212> TYPE: DNA
<213> ORGANISM: Streptococcus pneumoniae

<400> SEQUENCE: 7
atgaaattta gtaaaaaata tatagcagct ggatcagctg ttatcgtatc cttgagtcta     60
tgtgcctatg cactaaacca gcatcgttcg caggaaaata aggacaataa tcgtgtctct    120
tatgtggatg gcagccagtc aagtcagaaa agtgaaaact tgacaccaga ccaggttagc    180
cagaaagaag gaattcaggc tgagcaaatt gtaatcaaaa ttacagatca gggctatgta    240
acgtcacacg gtgaccacta tcattactat aatgggaaag ttccttatga tgccctcttt    300
agtgaagaac tcttgatgaa ggatccaaac tatcaactta aagacgctga tattgtcaat    360
gaagtcaagg gtggttatat catcaaggtc gatggaaaat attatgtcta cctgaaagat    420
gcagctcatg ctgataatgt tcgaactaaa gatgaaatca atcgtcaaaa acaagaacat    480
gtcaaagata atgagaaggt taactctaat gttgctgtag caaggtctca gggacgatat    540
acgacaaatg atggttatgt ctttaatcca gctgatatta tcgaagatac gggtaatgct    600
tatatcgttc ctcatggagg tcactatcac tacattccca aaagcgattt atctgctagt    660
gaattagcag cagctaaagc acatctggct ggaaaaaata tgcaaccgag tcagttaagc    720
tattcttcaa cagctagtga caataacacg caatctgtag caaaaggatc aactagcaag    780
ccagcaaata aatctgaaaa tctccagagt cttttgaagg aactctatga ttcacctagc    840
gcccaacgtt acagtgaatc agatggcctg gtctttgacc ctgctaagat tatcagtcgt    900
acaccaaatg gagttgcgat tccgcatggc gaccattacc actttattcc ttacagcaag    960
ctttctgcct tagaagaaaa gattgccaga atggtgccta tcagtggaac tggttctaca   1020
gtttctacaa atgcaaaacc taatgaagta gtgtctagtc taggcagtct ttcaagcaat   1080
ccttcttctt taacgacaag taaggagctc tcttcagcat ctgatggtta tatttttaat   1140
ccaaaagata tcgttgaaga aacggctaca gcttatattg taagacatgg tgatcatttc   1200
cattacattc caaaatcaaa tcaaattggg caaccgactc ttccaaacaa tagtctagca   1260
acaccttctc catctcttcc aatcaatcca ggaacttcac atgagaaaca tgaagaagat   1320
ggatacggat ttgatgctaa tcgtattatc gctgaagatg aatcaggttt tgtcatgagt   1380
cacggagacc acaatcatta tttcttcaag aaggacttga cagaagagca aattaaggtg   1440
cgcaaaaaca tttag                                                     1455

<210> SEQ ID NO 8
<211> LENGTH: 819
<212> TYPE: PRT
<213> ORGANISM: Streptococcus pneumoniae

<400> SEQUENCE: 8

Met Lys Ile Asn Lys Lys Tyr Leu Val Gly Ser Ala Ala Ala Leu Ile
  1               5                  10                  15

Leu Ser Val Cys Ser Tyr Glu Leu Gly Leu Tyr Gln Ala Arg Thr Val

-continued

```
            20                  25                  30

Lys Glu Asn Asn Arg Val Ser Tyr Ile Asp Gly Lys Gln Ala Thr Gln
        35                  40                  45

Lys Thr Glu Asn Leu Thr Pro Asp Glu Val Ser Lys Arg Glu Gly Ile
    50                  55                  60

Asn Ala Glu Gln Ile Val Ile Lys Ile Thr Asp Gln Gly Tyr Val Thr
65                  70                  75                  80

Ser His Gly Asp His Tyr His Tyr Tyr Asn Gly Lys Val Pro Tyr Asp
                85                  90                  95

Ala Ile Ile Ser Glu Glu Leu Leu Met Lys Asp Pro Asn Tyr Lys Leu
            100                 105                 110

Lys Asp Glu Asp Ile Val Asn Glu Val Lys Gly Gly Tyr Val Ile Lys
        115                 120                 125

Val Asp Gly Lys Tyr Tyr Val Tyr Leu Lys Asp Ala Ala His Ala Asp
    130                 135                 140

Asn Val Arg Thr Lys Glu Glu Ile Asn Arg Gln Lys Gln Glu His Ser
145                 150                 155                 160

Gln His Arg Glu Gly Gly Thr Pro Arg Asn Asp Gly Ala Val Ala Leu
                165                 170                 175

Ala Arg Ser Gln Gly Arg Tyr Thr Thr Asp Asp Gly Tyr Ile Phe Asn
            180                 185                 190

Ala Ser Asp Ile Ile Glu Asp Thr Gly Asp Ala Tyr Ile Val Pro His
        195                 200                 205

Gly Asp His Tyr His Tyr Ile Pro Lys Asn Glu Leu Ser Ala Ser Glu
    210                 215                 220

Leu Ala Ala Ala Glu Ala Phe Leu Ser Gly Arg Gly Asn Leu Ser Asn
225                 230                 235                 240

Ser Arg Thr Tyr Arg Arg Gln Asn Ser Asp Asn Thr Ser Arg Thr Asn
                245                 250                 255

Trp Val Pro Ser Val Ser Asn Pro Gly Thr Thr Asn Thr Asn Thr Ser
            260                 265                 270

Asn Asn Ser Asn Thr Asn Ser Gln Ala Ser Gln Ser Asn Asp Ile Asp
        275                 280                 285

Ser Leu Leu Lys Gln Leu Tyr Lys Leu Pro Leu Ser Gln Arg His Val
    290                 295                 300

Glu Ser Asp Gly Leu Val Phe Asp Pro Ala Gln Ile Thr Ser Arg Thr
305                 310                 315                 320

Ala Arg Gly Val Ala Val Pro His Gly Asp His Tyr His Phe Ile Pro
                325                 330                 335

Tyr Ser Gln Met Ser Glu Leu Glu Glu Arg Ile Ala Arg Ile Ile Pro
            340                 345                 350

Leu Arg Tyr Arg Ser Asn His Trp Val Pro Asp Ser Arg Pro Glu Gln
        355                 360                 365

Pro Ser Pro Gln Pro Thr Pro Glu Pro Ser Pro Gly Pro Gln Pro Ala
    370                 375                 380

Pro Asn Leu Lys Ile Asp Ser Asn Ser Ser Leu Val Ser Gln Leu Val
385                 390                 395                 400

Arg Lys Val Gly Glu Gly Tyr Val Phe Glu Glu Lys Gly Ile Ser Arg
                405                 410                 415

Tyr Val Phe Ala Lys Asp Leu Pro Ser Glu Thr Val Lys Asn Leu Glu
            420                 425                 430

Ser Lys Leu Ser Lys Gln Glu Ser Val Ser His Thr Leu Thr Ala Lys
        435                 440                 445
```

-continued

```
Lys Glu Asn Val Ala Pro Arg Asp Gln Glu Phe Tyr Asp Lys Ala Tyr
    450                 455                 460

Asn Leu Leu Thr Glu Ala His Lys Ala Leu Phe Glu Asn Lys Gly Arg
465                 470                 475                 480

Asn Ser Asp Phe Gln Ala Leu Asp Lys Leu Leu Glu Arg Leu Asn Asp
                485                 490                 495

Glu Ser Thr Asn Lys Glu Lys Leu Val Asp Asp Leu Leu Ala Phe Leu
            500                 505                 510

Ala Pro Ile Thr His Pro Glu Arg Leu Gly Lys Pro Asn Ser Gln Ile
        515                 520                 525

Glu Tyr Thr Glu Asp Glu Val Arg Ile Ala Gln Leu Ala Asp Lys Tyr
    530                 535                 540

Thr Thr Ser Asp Gly Tyr Ile Phe Asp Glu His Asp Ile Ile Ser Asp
545                 550                 555                 560

Glu Gly Asp Ala Tyr Val Thr Pro His Met Gly His Ser His Trp Ile
                565                 570                 575

Gly Lys Asp Ser Leu Ser Asp Lys Glu Lys Val Ala Ala Gln Ala Tyr
            580                 585                 590

Thr Lys Glu Lys Gly Ile Leu Pro Pro Ser Pro Asp Ala Asp Val Lys
        595                 600                 605

Ala Asn Pro Thr Gly Asp Ser Ala Ala Ala Ile Tyr Asn Arg Val Lys
    610                 615                 620

Gly Glu Lys Arg Ile Pro Leu Val Arg Leu Pro Tyr Met Val Glu His
625                 630                 635                 640

Thr Val Glu Val Lys Asn Gly Asn Leu Ile Ile Pro His Lys Asp His
                645                 650                 655

Tyr His Asn Ile Lys Phe Ala Trp Phe Asp Asp His Thr Tyr Lys Ala
            660                 665                 670

Pro Asn Gly Tyr Thr Leu Glu Asp Leu Phe Ala Thr Ile Lys Tyr Tyr
        675                 680                 685

Val Glu His Pro Asp Glu Arg Pro His Ser Asn Asp Gly Trp Gly Asn
    690                 695                 700

Ala Ser Glu His Val Leu Gly Lys Lys Asp His Ser Glu Asp Pro Asn
705                 710                 715                 720

Lys Asn Phe Lys Ala Asp Glu Glu Pro Val Glu Glu Thr Pro Ala Glu
                725                 730                 735

Pro Glu Val Pro Gln Val Glu Thr Glu Lys Val Glu Ala Gln Leu Lys
            740                 745                 750

Glu Ala Glu Val Leu Leu Ala Lys Val Thr Asp Ser Ser Leu Lys Ala
        755                 760                 765

Asn Ala Thr Glu Thr Leu Ala Gly Leu Arg Asn Asn Leu Thr Leu Gln
    770                 775                 780

Ile Met Asp Asn Asn Ser Ile Met Ala Glu Ala Glu Lys Leu Leu Ala
785                 790                 795                 800

Leu Leu Lys Gly Ser Asn Pro Ser Ser Val Ser Lys Glu Lys Ile Asn
                805                 810                 815

Lys Leu Asn
```

<210> SEQ ID NO 9
<211> LENGTH: 2451
<212> TYPE: DNA
<213> ORGANISM: Streptococcus pneumoniae
<220> FEATURE:
<221> NAME/KEY: misc_feature -continued
<222> LOCATION: (1)..(2451)
<223> OTHER INFORMATION: n = a, c, t or g

<400> SEQUENCE: 9
atgaaaatta ataagaaata ccttgttggt tctgcggcag ctttgatttt aagtgtttgt 60
tcttacgagt tgggactgta tcaagctaga acggttaagg aaaataatcg tgtttcctat 120
atagatggaa aacaagcgac gcaaaaaacg gagaatttga ctcctgatga ggttagcaag 180
cgtgaaggaa tcaatgctga gcaaatcgtc atcaagataa cagaccaagg ctatgtcact 240
tcacatggcg accactatca ttattacaat ggtaaggttc cttatgacgc tatcatcagt 300
gaagaattac tcatgaaaga tccaaactat aagctaaaag atgaggatat tgttaatgag 360
gtcaagggtg gatatgttat caaggtagat ggaaaatact atgtttacct taaggatgct 420
gcccacgcgg ataacgtccg tacaaaagag gaaatcaatc gacaaaaaca agagcatagt 480
caacatcgtg aaggtggaac tccaagaaac gatggtgctg ttgccttggc acgttcgcaa 540
ggacgctata ctacagatga tggttatatc tttaatgctt ctgatatcat agaggatact 600
ggtgatgctt atatcgttcc tcatggagat cattaccatt acattcctaa gaatgagtta 660
tcagctagcg agttggctgc tgcagaagcc ttcctatctg gtcgaggaaa tctgtcaaat 720
tcaagaacct atcgccgaca aaatagcgat aacacttcaa gaacaaactg ggtaccttct 780
gtaagcaatc caggaactac aaatactaac acaagcaaca acagcaacac taacagtcaa 840
gcaagtcaaa gtaatgacat tgatagtctc ttgaaacagc tctacaaact gcctttgagt 900
caacgacatg tagaatctga tggccttgtc tttgatccag cacaaatcac aagtcgaaca 960
gctagaggtg ttgcagtgcc acacggagat cattaccact tcatccctta ctctcaaatg 1020
tctgaattgg aagaacgaat cgctcgtatt attcccccttc gttatcgttc aaaccattgg 1080
gtaccagatt caaggccaga acaaccaagt ccacaaccga ctccggaacc tagtccaggc 1140
ccgcaacctg caccaaatct taaaatagac tcaaattctt ctttggttag tcagctggta 1200
cgaaaagttg gggaaggata tgtattcgaa gaaaagggca tctctcgtta tgtctttgcg 1260
aaagatttac catctgaaac tgttaaaaat cttgaaagca agttatcaaa acaagagagt 1320
gtttcacaca ctttaactgc taaaaaagaa aatgttgctc ctcgtgacca agaattttat 1380
gataaagcat ataatctgtt aactgaggct cataaagcct tgtttgnaaa taagggtcgt 1440
aattctgatt tccaagcctt agacaaatta ttagaacgct tgaatgatga atcgactaat 1500
aaagaaaaat tggtagatga tttattggca ttcctagcac caattaccca tccagagcga 1560
cttggcaaac caaattctca aattgagtat actgaagacg aagttcgtat tgctcaatta 1620
gctgataagt atacaacgtc agatggttac atttttgatg aacatgatat aatcagtgat 1680
gaaggagatg catatgtaac gcctcatatg ggccatagtc actggattgg aaaagatagc 1740
ctttctgata aggaaaaagt tgcagctcaa gcctatacta aagaaaaagg tatcctacct 1800
ccatctccag acgcagatgt taaagcaaat ccaactggag atagtgcagc agctatttac 1860
aatcgtgtga aaggggaaaa acgaattcca ctcgttcgac ttccatatat ggttgagcat 1920
acagttgagg ttaaaaacgg taatttgatt attcctcata aggatcatta ccataatatt 1980
aaatttgctt ggtttgatga tcacacatac aaagctccaa atggctatac cttggaagat 2040
ttgtttgcga cgattaagta ctacgtagaa caccctgacg aacgtccaca ttctaatgat 2100
ggatggggca atgccagtga gcatgtgtta ggcaagaaag accacagtga agatccaaat 2160
aagaacttca aagcggatga agagccagta gaggaaacac ctgctgagcc agaagtccct 2220

-continued

```
caagtagaga ctgaaaaagt agaagcccaa ctcaaagaag cagaagtttt gcttgcgaaa   2280

gtaacggatt ctagtctgaa agccaatgca acagaaactc tagctggttt acgaaataat   2340

ttgactcttc aaattatgga taacaatagt atcatggcag aagcagaaaa attacttgcg   2400

ttgttaaaag gaagtaatcc ttcatctgta agtaaggaaa aaataaacta a            2451
```

```
<210> SEQ ID NO 10
<211> LENGTH: 819
<212> TYPE: PRT
<213> ORGANISM: Streptococcus pneumoniae

<400> SEQUENCE: 10

Met Lys Ile Asn Lys Lys Tyr Leu Ala Gly Ser Val Ala Val Leu Ala
  1               5                  10                  15

Leu Ser Val Cys Ser Tyr Glu Leu Gly Arg Tyr Gln Ala Gly Gln Asp
             20                  25                  30

Lys Lys Glu Ser Asn Arg Val Ala Tyr Ile Asp Gly Asp Gln Ala Gly
         35                  40                  45

Gln Lys Ala Glu Asn Leu Thr Pro Asp Glu Val Ser Lys Arg Glu Gly
     50                  55                  60

Ile Asn Ala Glu Gln Ile Val Ile Lys Ile Thr Asp Gln Gly Tyr Val
 65                  70                  75                  80

Thr Ser His Gly Asp His Tyr His Tyr Tyr Asn Gly Lys Val Pro Tyr
                 85                  90                  95

Asp Ala Ile Ile Ser Glu Glu Leu Leu Met Lys Asp Pro Asn Tyr Gln
            100                 105                 110

Leu Lys Asp Ser Asp Ile Val Asn Glu Ile Lys Gly Gly Tyr Val Ile
        115                 120                 125

Lys Val Asn Gly Lys Tyr Tyr Val Tyr Leu Lys Asp Ala Ala His Ala
    130                 135                 140

Asp Asn Ile Arg Thr Lys Glu Glu Ile Lys Arg Gln Lys Gln Glu Arg
145                 150                 155                 160

Ser His Asn His Asn Ser Arg Ala Asp Asn Ala Val Ala Ala Ala Arg
                165                 170                 175

Ala Gln Gly Arg Tyr Thr Thr Asp Asp Gly Tyr Ile Phe Asn Ala Ser
            180                 185                 190

Asp Ile Ile Glu Asp Thr Gly Asp Ala Tyr Ile Val Pro His Gly Asp
        195                 200                 205

His Tyr His Tyr Ile Pro Lys Asn Glu Leu Ser Ala Ser Glu Leu Ala
    210                 215                 220

Ala Ala Glu Ala Tyr Trp Asn Gly Lys Gln Gly Ser Arg Pro Ser Ser
225                 230                 235                 240

Ser Ser Ser Tyr Asn Ala Asn Pro Ala Gln Pro Arg Leu Ser Glu Asn
                245                 250                 255

His Asn Leu Thr Val Thr Pro Thr Tyr His Gln Asn Gln Gly Glu Asn
            260                 265                 270

Ile Ser Ser Leu Leu Arg Glu Leu Tyr Ala Lys Pro Leu Ser Glu Arg
        275                 280                 285

His Val Glu Ser Asp Gly Leu Ile Phe Asp Pro Ala Gln Ile Thr Ser
    290                 295                 300

Arg Thr Ala Arg Gly Val Ala Val Pro His Gly Asn His Tyr His Phe
305                 310                 315                 320

Ile Pro Tyr Glu Gln Met Ser Glu Leu Glu Lys Arg Ile Ala Arg Ile
                325                 330                 335
```

-continued

```
Ile Pro Leu Arg Tyr Arg Ser Asn His Trp Val Pro Asp Ser Arg Pro
            340                 345                 350

Glu Glu Pro Ser Pro Gln Pro Thr Pro Glu Pro Ser Pro Ser Pro Gln
        355                 360                 365

Pro Ala Pro Ser Asn Pro Ile Asp Gly Lys Leu Val Lys Glu Ala Val
    370                 375                 380

Arg Lys Val Gly Asp Gly Tyr Val Phe Glu Glu Asn Gly Val Ser Arg
385                 390                 395                 400

Tyr Ile Pro Ala Lys Asp Leu Ser Ala Glu Thr Ala Ala Gly Ile Asp
                405                 410                 415

Ser Lys Leu Ala Lys Gln Glu Ser Leu Ser His Lys Leu Gly Thr Lys
            420                 425                 430

Lys Thr Asp Leu Pro Ser Ser Asp Arg Glu Phe Tyr Asn Lys Ala Tyr
        435                 440                 445

Asp Leu Leu Ala Arg Ile His Gln Asp Leu Leu Asp Asn Lys Gly Arg
    450                 455                 460

Gln Val Asp Phe Glu Ala Leu Asp Asn Leu Leu Glu Arg Leu Lys Asp
465                 470                 475                 480

Val Ser Ser Asp Lys Val Lys Leu Val Glu Asp Ile Leu Ala Phe Leu
                485                 490                 495

Ala Pro Ile Arg His Pro Glu Arg Leu Gly Lys Pro Asn Ala Gln Ile
            500                 505                 510

Thr Tyr Thr Asp Asp Glu Ile Gln Val Ala Lys Leu Ala Gly Lys Tyr
        515                 520                 525

Thr Ala Glu Asp Gly Tyr Ile Phe Asp Pro Arg Asp Ile Thr Ser Asp
    530                 535                 540

Glu Gly Asp Ala Tyr Val Thr Pro His Met Thr His Ser His Trp Ile
545                 550                 555                 560

Lys Lys Asp Ser Leu Ser Glu Ala Glu Arg Ala Ala Ala Gln Ala Tyr
                565                 570                 575

Ala Glu Glu Lys Gly Leu Thr Pro Pro Ser Thr Asp His Gln Asp Ser
            580                 585                 590

Gly Asn Thr Glu Ala Lys Gly Ala Glu Ala Ile Tyr Asn Arg Val Lys
        595                 600                 605

Ala Ala Lys Lys Val Pro Leu Asp Arg Met Pro Tyr Asn Leu Gln Tyr
    610                 615                 620

Thr Val Glu Val Lys Asn Gly Ser Leu Ile Ile Pro His Tyr Asp His
625                 630                 635                 640

Tyr His Asn Ile Lys Phe Glu Trp Phe Asp Glu Gly Leu Tyr Glu Ala
                645                 650                 655

Pro Lys Gly Tyr Thr Leu Glu Asp Leu Leu Ala Thr Val Lys Tyr Tyr
            660                 665                 670

Val Glu His Pro Asn Glu Arg Pro His Ser Asp Asn Gly Phe Gly Asn
        675                 680                 685

Ala Ser Asp His Val Gln Arg Asn Lys Asn Gly Gln Ala Asp Thr Asn
    690                 695                 700

Gln Thr Glu Lys Pro Ser Glu Glu Lys Pro Gln Thr Glu Lys Pro Glu
705                 710                 715                 720

Glu Glu Thr Pro Arg Glu Glu Lys Pro Gln Ser Glu Lys Pro Glu Ser
                725                 730                 735

Pro Lys Pro Thr Glu Glu Pro Glu Glu Ser Pro Glu Glu Ser Glu Glu
            740                 745                 750

Pro Gln Val Glu Thr Glu Lys Val Glu Glu Lys Leu Arg Glu Ala Glu
```

-continued

```
        755                 760                 765

Asp Leu Leu Gly Lys Ile Gln Asp Pro Ile Ile Lys Ser Asn Ala Lys
    770                 775                 780

Glu Thr Leu Thr Gly Leu Lys Asn Asn Leu Leu Phe Gly Thr Gln Asp
785                 790                 795                 800

Asn Asn Thr Ile Met Ala Glu Ala Glu Lys Leu Leu Ala Leu Leu Lys
                805                 810                 815

Glu Ser Lys

<210> SEQ ID NO 11
<211> LENGTH: 2531
<212> TYPE: DNA
<213> ORGANISM: Streptococcus pneumoniae

<400> SEQUENCE: 11

atgaaaatta ataaaaaata tctagcaggt tcagtggcag tccttgccct aagtgtttgt      60

tcctatgagc ttggacgtta ccaagctggt caggataaga aagagtctaa tcgagttgct     120

tatatagatg gtgatcaggc tggtcaaaag gcagaaaact tgacaccaga tgaagtcagt     180

aagagggagg ggatcaacgc cgaacaaatt gttatcaaga ttacggatca aggttatgtg     240

acctctcatg gagaccatta tcattactat aatggcaagg ttccttatga tgccatcatc     300

agtgaagagc tcctcatgaa agatccgaat tatcagttga aggattcaga cattgtcaat     360

gaaatcaagg gtggttatgt cattaaggta aacggtaaat actatgttta ccttaaggat     420

gcrgctcatg cggataatat tcggacaaaa gaagagatta aacgtcagaa gcaggaacgc     480

agtcataatc ataactcaag agcagataat gctgttgctg cagccagagc ccaaggacgt     540

tatacaacgg atgatgggta tatcttcaat gcatctgata tcattgagga cacgggtgat     600

gcttatatcg ttcctcacgg cgaccattac cattacattc ctaagaatga gttatcagct     660

agcgagttag ctgctgcaga agcctattgg aatgggaagc agggatctcg tccttcttca     720

agttctagtt ataatgcaaa tccagctcaa ccaagattgt cagagaacca caatctgact     780

gtcactccaa cttatcatca aaatcaaggg gaaaacattt caagcctttt acgtgaattg     840

tatgctaaac ccttatcaga acgccatgtg gaatctgatg gccttatttt cgacccagcg     900

caaatcacaa gtcgaaccgc cagaggtgta gctgtccctc atggtaacca ttaccacttt     960

atcccttatg aacaaatgtc tgaattggaa aaacgaattg ctcgtattat tccccttcgt    1020

tatcgttcaa accattgggt accagattca agaccagaag aaccaagtcc acaaccgact    1080

ccagaaccta gtccaagtcc gcaaccagct ccaagcaatc caattgatgg gaaattggtc    1140

aaagaagctg ttcgaaaagt aggcgatggt tatgtctttg aggagaatgg agtttctcgt    1200

tatatcccag ccaaggatct ttcagcagaa acagcagcag gcattgatag caaactggcc    1260

aagcaggaaa gtttatctca taagctagga actaagaaaa ctgacctccc atctagtgat    1320

cgagaatttt acaataaggc ttatgactta ctagcaagaa ttcaccaaga tttacttgat    1380

aataaaggtc gacaagttga ttttgaggct ttggataacc tgttggaacg actcaaggat    1440

gtctcaagtg ataaagtcaa gttagtggaa gatattcttg ccttcttagc tccgattcgt    1500

catccagaac gtttaggaaa accaaatgcg caaattacct acactgatga tgagattcaa    1560

gtagccaagt tggcaggcaa gtacacagca gaagacggtt atatctttga tcctcgtgat    1620

ataaccagtg atgaggggga tgcctatgta actccacata tgacccatag ccactggatt    1680

aaaaaagata gtttgtctga agctgagaga gcggcagccc aggcttatgc traagagaaa    1740
```

-continued

```
ggtttgaccc ctccttcgac agaccatcag gattcaggaa atactgaggc aaaaggagca   1800

gaagctatct acaaccgmgt gaaagcagct aagaaggtgc cacttgatcg tatgccttac   1860

aatcttcaat atactgtaga agtcaaaaac ggtagtttaa tcatacctca ttatgaccat   1920

taccataaca tcaaatttga gtggtttgac gaaggccttt atgaggcacc taaggggtat   1980

actcttgagg atcttttggc gactgtcaag tactatgtcg aacatccaaa cgaacgtccg   2040

cattcagata atggttttgg taacgctagc gaccatgttc aaagaaacaa aaatggtcaa   2100

gctgatacca atcaaacgga aaaaccaagc gaggagaaac ctcagacaga aaaacctgag   2160

gaagaaaccc ctcgagaaga gaaaccgcaa agcgagaaac cagagtctcc aaaaccaaca   2220

gaggaaccag aagaatcacc agaggaatca gaagaacctc aggtcgagac tgaaaaggtt   2280

gaagaaaaac tgagagaggc tgaagattta cttggaaaaa tccaggatcc aattatcaag   2340

tccaatgcca aagagactct cacaggatta aaaaataatt tactatttgg cacccaggac   2400

aacaatacta ttatggcaga agctgaaaaa ctattggctt tattaaagga gagtaagtaa   2460

aggtagaagc ttaagggcga atttggcacc caggacaaca atactattat ggcagaagct   2520

gaaaaactat t                                                        2531


<210> SEQ ID NO 12
<211> LENGTH: 6
<212> TYPE: PRT
<213> ORGANISM: Artificial Sequence
<220> FEATURE:
<221> NAME/KEY: VARIANT
<222> LOCATION: (1)..(6)
<223> OTHER INFORMATION: Xaa = any amino acid

<400> SEQUENCE: 12

His Xaa Xaa His Xaa His
  1               5


<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Substrate
      sequence for Type II Signal Peptidase.

<400> SEQUENCE: 13

Leu Ser Val Cys
  1


<210> SEQ ID NO 14
<211> LENGTH: 4
<212> TYPE: PRT
<213> ORGANISM: Artificial Sequence
<220> FEATURE:
<221> NAME/KEY: VARIANT
<222> LOCATION: (2)..(3)
<223> OTHER INFORMATION: Xaa = any amino acid

<400> SEQUENCE: 14

Leu Xaa Xaa Cys
  1
```

VACCINE COMPOSITIONS COMPRISING *STREPTOCOCCUS PNEUMONIAE* POLYPEPTIDES HAVING SELECTED STRUCTURAL MOTIFS

This application is based on U.S. Provisional Application No. 60/113,048, filed Dec. 21, 1998, which is hereby incorporated in its entirety.

FIELD OF THE INVENTION

This invention relates generally to the field of bacterial antigens and their use, for example, as immunogenic agents in humans and animals to stimulate an immune response. More specifically, it relates to the vaccination of mammalian species with a polypeptide comprising at least one conserved histidine triad residue (HxxHxH-SEQ ID NO: 12) and at least one helix-forming polypeptide obtained from *Streptococcus pneumoniae* as a mechanism for stimulating production of antibodies that protect the vaccine recipient against infection by a wide range of serotypes of pathogenic *S. pneumoniae*. Further, the invention relates to antibodies against such polypeptides useful in diagnosis and passive immune therapy with respect to diagnosing and treating such pneumococcal infections.

In a particular aspect, the present invention relates to the prevention and treatment of pneumococcal infections such as infections of the middle ear, nasopharynx, lung and bronchial areas, blood, CSF, and the like, that are caused by pneumococcal bacteria.

BACKGROUND OF THE INVENTION

*Streptococcus pneumoniae* is a gram positive bacteria which is a major causative agent in invasive infections in animals and humans, such as sepsis, meningitis, otitis media and lobar pneumonia (Tuomanen et al. *New Engl. J. Med.* 322:1280–1284 (1995)). As part of the infective process, peumococci readily bind to non-inflamed human epithelial cells of the upper and lower respiratory tract by binding to eukaryotic carbohydrates in a lectin-like manner (Cundell et al., *Micro. Path.* 17:361–374 (1994)). Conversion to invasive pneumococcal infections for bound bacteria may involve the local generation of inflammatory factors which may activate the epithelial cells to change the number and type of receptors on their surface (Cundell et al., *Nature*, 377:435–438 (1995)). Apparently, one such receptor, platelet activating factor (PAF) is engaged by the pneumococcal bacteria and within a very short period of time (minutes) from the appearance of PAF, pneumococci exhibit strongly enhanced adherence and invasion of tissue. Certain soluble receptor analogs have been shown to prevent the progression of pneumococcal infections (Idanpaan-Heikkila et al., *J. Inf. Dis.*, 176:704–712 (1997)). A number of various other proteins have been suggested as being involved in the pathogenicity of *S. pneumoniae*. There remains a need for identifying polypeptides having epitopes in common from various strains of *S. pneumoniae* in order to utilize such polypeptides as vaccines to provide protection against a wide variety of *S. pneumoniae*.

SUMMARY OF INVENTION

In accordance with the present invention, there is provided vaccines and vaccine compositions that include polypeptides obtained from *S. pneumoniae* and/or variants of said polypeptides and/or active fragments of such polypeptides.

The active fragments, as hereinafter defined, include a histidine triad residue(s) and/or coiled coil regions of such polypeptides.

The term "percent identity" or "percent identical," when referring to a sequence, means that a sequence is compared to a claimed or described sequence from an alignment of the sequence to be compared (the "Compared Sequence") with the described or claimed sequence (the "Reference Sequence"). The percent identity is determined as follows:

$$\text{Percent Identity}=[1-(C/R)]100$$

wherein C is the number of differences between the Reference Sequence and the Compared Sequence over the length of the alignment between the Compared Sequence and the Reference Sequence wherein (i) each base or amino acid in the Reference Sequence that does not have an aligned base or amino acid in the Compared Sequence and (ii) each gap in the Reference Sequence and (iii) each aligned base or amino acid in the Reference Sequence that is different from an aligned base or amino acid in the Compared Sequence, each being a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence in which the Percent Identity as calculated above is about equal to or greater than a specified minimum Percent Identity then the Compared Sequence has the specified minimum Percent Identity to the Reference Sequence even though alignments may exist in which the hereinabove calculated Percent Identity is less than the specified Percent Identity.

"Isolated" in the context of the present invention with respect to polypeptides and/or polynucleotides means that the material is removed from its original environment (e.g., the natural environment if it is naturally occurring). For example, a naturally-occurring polynucleotide or polypeptide present in a living organism is not isolated, but the same polynucleotide or polypeptide, separated from some or all of the co-existing materials in the natural system, is isolated. Such polynucleotides could be part of a vector and/or such polynucleotides or polypeptides could be part of a composition, and still be isolated in that such vector or composition is not part of its natural environment. The polypeptides and polynucleotides of the present invention are preferably provided in an isolated form, and preferably are purified to homogeneity.

BRIEF DESCRIPTION OF DRAWINGS

FIG. 2A shows that one hundred percent of the mice immunized with the SP36 antiserum survived the 21-day observation period after challenge with 172 CFU of strain SJ2 (serotype 6B). Eighty percent of the mice immunized with a control serum (rabbit anti-FimC) died by day 8, and ninety percent died by day 12. FIG. 2B shows that 90 percent of the mice immunized with the Sp36 antiserum survived the 8-day observation after challenge with 862 CFU of strain EF6796 (serotype 6A). Ninety percent of the mice immunized with a control serum (collected before immunization) died by day 5.

FIG. 6 is an amino acid alignment comparison of four related pneumococcal proteins, namely Sp36A (PhtA; SEQ ID NO:8), Sp36B (PhtB; SEQ ID NO:10), Sp36D (PhtD; SEQ ID NO:4), Sp36E (PhtE; SEQ ID NO:6), respectively. Dashes in a sequence indicate gaps introduced to maximize the sequence similarity. Amino acid residues that match are boxed.

Figure 7R:
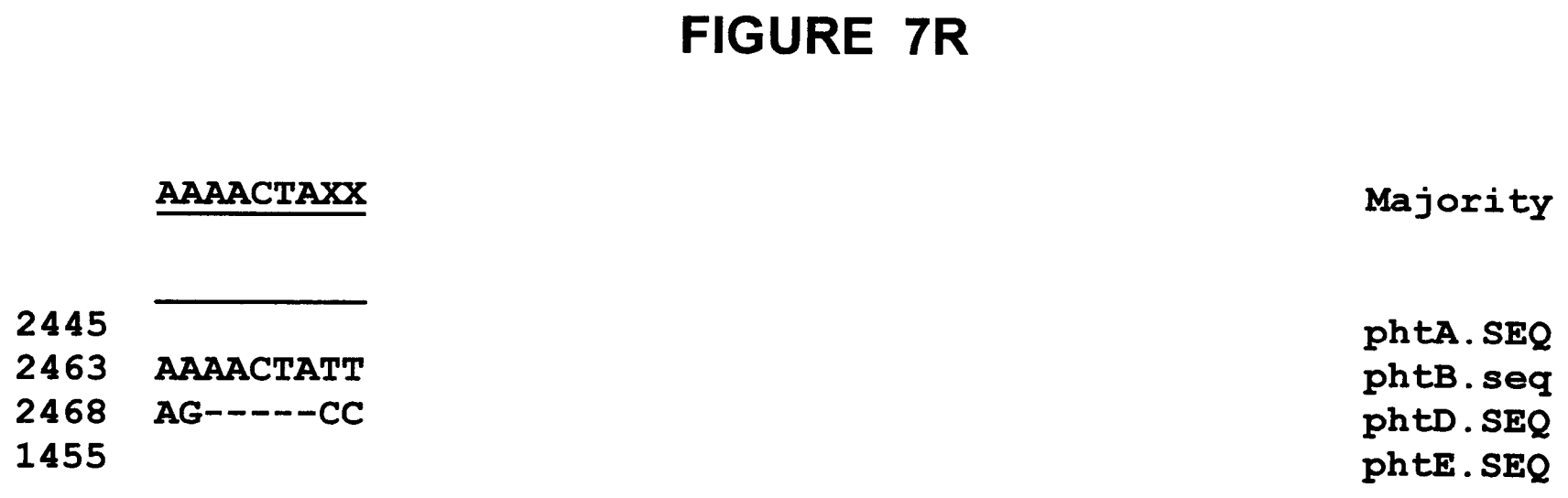

FIG. 7 is a nucleotide alignment comparison of four related pneumococcal genes, namely Sp36A (PhtA; SEQ ID NO:9), Sp36B (PhtB; SEQ ID NO:11), Sp36D (PhtD; SEQ ID NO:5), Sp36E (PhtE; SEQ ID NO:7), respectively. Dashes in a sequence indicate gaps introduced to maximize the sequence similarity.

SUMMARY OF THE INVENTION

Figure 1:
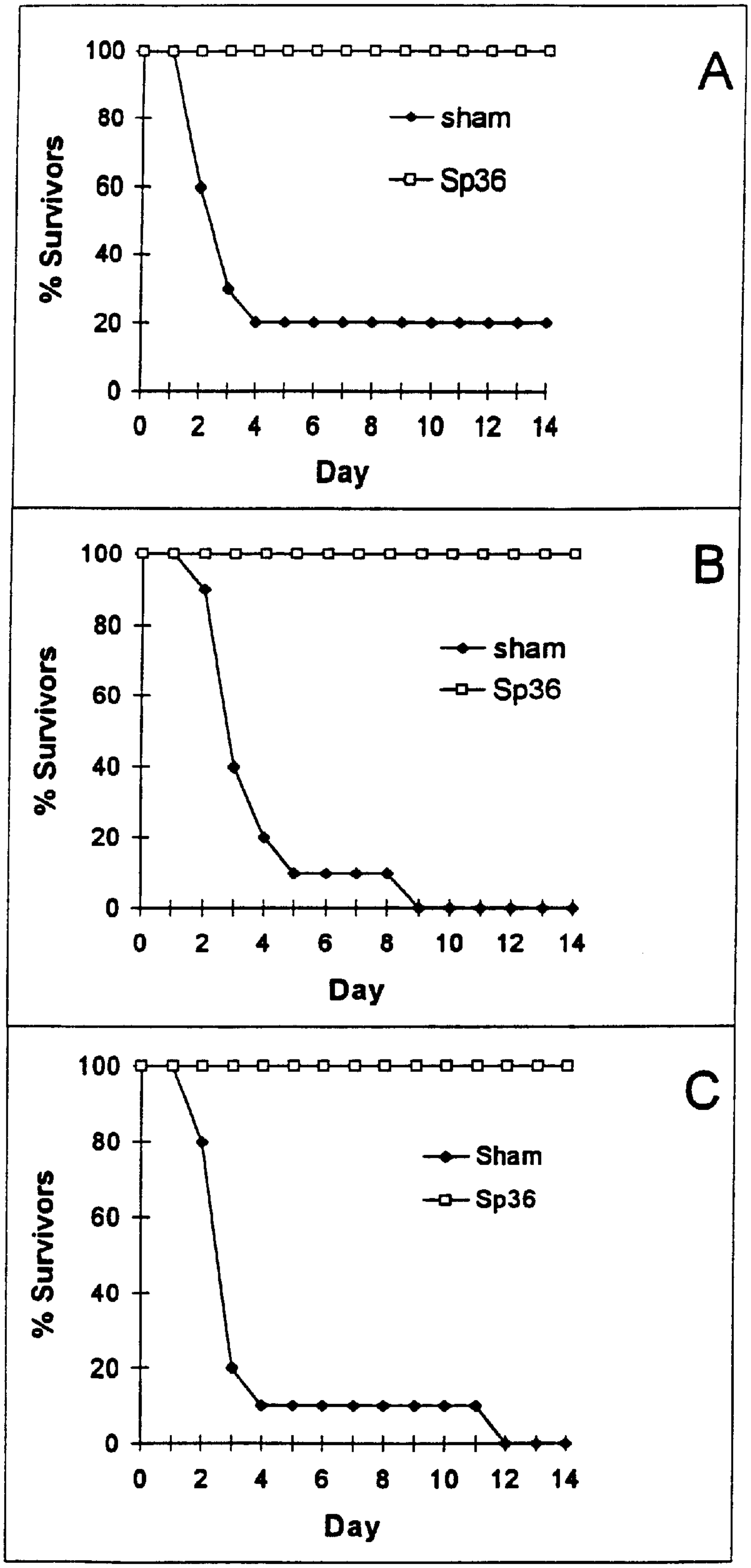
FIGS. 1A–1C, respectively, report the results of three experiments using different preparations of SP36. The results demonstrate that active immunization with recombinant SP36 derived from pneumococcal strain Norway serotype 4 is able to protect mice from death in a model of pneumococcal sepsis using a heterologous strain, SJ2 (serotype 6B). In each of the three experiments shown, one hundred percent of the mice immunized with SP36 survived for the 14-day observation period following challenge with approximately 500 cfu of pneumococci, while eighty to one hundred percent of sham-immunized mice (injected with PBS and adjuvant) died during the same period.

In accordance with one aspect of the present invention, there is provided a vaccine, generally in the form of a composition, that includes at least one polypeptide that is at least 90% identical to (c) a polypeptide sequence comprising amino acids 20–838 of SEQ ID NO:4 or (ii) a polypeptide sequence comprising amino acids 21–480 of SEQ ID NO:6 or an active fragment of the foregoing.

In accordance with another aspect of the present invention, there is provided a vaccine, generally in the form of a composition, that includes an active fragment of a polypeptide that is at least 90% identical to (i) a polypeptide comprising amino acids 20–819 of SEQ ID NO:8 or (ii) a polypeptide comprising amino acids 20–819 of SEQ ID NO:10.

The term "active fragment" means a fragment that includes one or more histidine triad residues and/or one or more coiled coil regions. A "histidine triad residue" is the portion of the polypeptide that has the sequence HxxHxH (SEQ ID NO: 12) wherein H is histidine and x is an amino acid other than histidine.

A coiled coil region is the region predicted by "Coils" algorithm: Lupas, A., Van Dyke, M., and Stock, J. (1991) Predicting Coiled Coils from Protein Sequences, *Science* 252:1162–1164.

In accordance with one embodiment, the active fragment includes both one or more histidine triad residues and at least one coiled coil region of the applicable polypeptide sequence. In accordance with another embodiment, the active fragment includes at least two histidine triad residues.

In another embodiment, the active fragment that includes at least one histidine triad residue or at least one coiled-coil region of the applicable polypeptide includes at least about ten percent of the applicable polypeptide and no more than about 85% of the applicable polypeptide.

The polypeptide of SEQ ID NO:4 includes five histidine triad residues, as follows:

amino acids 83–88, 207–212, 315–320, 560–565, and 644–649.

The polypeptide of SEQ ID NO:6 includes five histidine triad residues, as follows:

amino acids 83–88, 205–210, 309–314, 396–401, and 461–466.

In addition, the polypeptide of SEQ ID NO:4 includes two coiled-coil regions (amino acids 139–159 and amino acids 769–791) and the polypeptide of SEQ ID NO:6 includes one coiled-coil region (amino acids 139–172).

The polypeptide of SEQ ID NO: 8 includes the following regions:

HxxHxH (SEQ ID NO: 12): amino acids 82–87, 208–213, 328–333, 569–574, and 653–658.

Coiled-coils: amino acids 137–164, 425–453, 481–512, and 743–770.

In accordance with a further aspect of the invention, a vaccine of the type hereinabove described is administered for the purpose of preventing or treating infection caused by *S. pneumoniae.*

A vaccine, or vaccine composition, in accordance with the present invention may include one or more of the hereinabove described polypeptides or active fragments thereof. When employing more than one polypeptide or active fragment, such two or more polypeptides and/or active fragments may be used as a physical mixture or as a fusion of two or more polypeptides or active fragments. The fusion fragment or fusion polypeptide may be produced, for example, by recombinant techniques or by the use of appropriate linkers for fusing previously prepared polypeptides or active fragments.

In an embodiment of the invention, there is provided (a) a polypeptide that is at least 95% identical or at least 97% identical or 100% identical to (i) a polypeptide sequence comprising amino acids 20–838 of SEQ ID NO:4 or (ii) a polypeptide sequence comprising amino acids 21–480 of SEQ ID NO:6; or (b) an active fragment of the polypeptide of (a).

In the case where the polypeptide is a variant of the polypeptide comprising the mature polypeptide of SEQ ID NO:4 or SEQ ID NO:6, or any of the active fragments of the invention, the variation in the polypeptide or fragment is generally in a portion thereof other than the histidine triad residues and the coiled-coil region, although variations in one or more of these regions may be made.

In many cases, the variation in the polypeptide or active fragment is a conservative amino acid substitution, although other substitutions are within the scope of the invention.

In accordance with the present invention, a polypeptide variant includes variants in which one or more amino acids are substituted and/or deleted and/or inserted.

In another aspect, the invention relates to passive immunity vaccines formulated from antibodies against a polypeptide or active fragment of a polypeptide of the present invention. Such passive immunity vaccines can be utilized to prevent and/or treat pneumococcal infections in patients. In this manner, according to a further aspect of the invention, a vaccine can be produced from a synthetic or recombinant polypeptide of the present invention or an antibody against such polypeptide.

In still another aspect the present invention relates to a method of using one or more antibodies (monoclonal, polyclonal or sera) to the polypeptides of the invention as described above for the prophylaxis and/or treatment of diseases that are caused by pneumococcal bacteria. In particular, the invention relates to a method for the prophylaxis and/or treatment of infectious diseases that are caused by *S. pneumoniae*. In a still further preferred aspect, the invention relates to a method for the prophylaxis and/or treatment of otitis media, nasopharyngeal, bronchial infections, and the like in humans by utilizing a vaccine of the present invention.

Generally, vaccines are prepared as injectables, in the form of aqueous solutions or suspensions. Vaccines in an oil base are also well known such as for inhaling. Solid forms which are dissolved or suspended prior to use may also be formulated. Pharmaceutical carriers are generally added that are compatible with the active ingredients and acceptable for pharmaceutical use. Examples of such carriers include, but are not limited to, water, saline solutions, dextrose, or glycerol. Combinations of carriers may also be used.

Vaccine compositions may further incorporate additional substances to stabilize pH, or to function as adjuvants, wetting agents. or emulsifying agents, which can serve to improve the effectiveness of the vaccine.

Vaccines are generally formulated for parental administration and are injected either subcutaneously or intramuscularly. Such vaccines can also be formulated as suppositories or for oral administration, using methods known in the art.

The amount of vaccine sufficient to confer immunity to pathogenic bacteria is determined by methods well known to those skilled in the art. This quantity will be determined based upon the characteristics of the vaccine recipient and the level of immunity required. Typically, the amount of vaccine to be administered will be determined based upon the judgment of a skilled physician. Where vaccines are administered by subcutaneous or intramuscular injection, a range of 50 to 500 $\mu$g purified protein may be given.

The present invention is also directed to a vaccine in which a polypeptide or active fragment of the present invention is delivered or administered in the form of a polynucleotide encoding the polypeptide or active fragment, whereby the polypeptide or active fragment is produced in vivo. The polynucleotide may be included in a suitable expression vector and combined with a pharmaceutically acceptable carrier.

In addition, the polypeptides of the present invention can be used as immunogens to stimulate the production of antibodies for use in passive immunotherapy, for use as diagnostic reagents, and for use as reagents in other processes such as affinity chromatography.

In another aspect the present invention provides polynucleotides which encode the hereinabove described polypeptides and active fragments of the invention. The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand.

In accordance with another aspect of the present invention, there is provided (A) an isolated polynucleotide that is at least 90% identical to a polynucleotide sequence encoding (i) a polypeptide comprising amino acids 20–838 of SEQ ID NO:4 or (ii) a polypeptide comprising amino acids 21–480 of SEQ ID NO:6, or (B) a fragment of the polynucleotide of (A) that encodes an active polypeptide fragment or (C) a polynucleotide that is at least 90% identical to a polynucleotide sequence encoding an active fragment of (i) a polypeptide comprising amino acids 20–819 of SEQ ID NO:8 or (ii) a polypeptide comprising amino acids 20–819 of SEQ ID NO:10.

In specific embodiments, the polynucleotide is at least 95% identical, preferably at least 97% identical, and even 100% identical to such polynucleotide sequence.

The term "polynucleotide encoding a polypeptide" encompasses a polynucleotide which includes only coding sequence for the polypeptide as well as a polynucleotide which includes additional coding and/or non-coding sequence.

The present invention further relates to variants of polynucleotides. The variants of the polynucleotides may be a naturally occurring allelic variant of the polynucleotides or a non-naturally occurring variant of the polynucleotides. The variants include variants in which one or more bases are substituted, deleted or inserted. Complements to such coding polynucleotides may be utilized to isolate polynucleotides encoding the same or similar polypeptides. In particular, such procedures are useful to obtain native immunogenic portions of polypeptides from different serotypes of *S. pneumoniae*, which is especially useful in the production of "chain" polypeptide vaccines containing multiple immunogenic segments.

SEQ ID NO:5 is a representative example of a polynucleotide encoding the polypeptide of SEQ ID NO:4 and SEQ ID NO:7 is a representative example of a polynucleotide encoding the polypeptide of SEQ ID NO:6. SEQ ID NO:9 is a representative example of a polynucleotide encoding the polypeptide of SEQ ID NO:8, and SEQ ID No:11 is a representative example of a polynucleotide encoding the polypeptide of SEQ ID NO:10. As a result of the known degeneracy of the genetic code, other polynucleotides that encode the polypeptides of SEQ ID NO:4, SEQ ID NO:6, SEQ ID NO:8 and SEQ ID NO:10 should be apparent to those skilled in the art from the teachings herein.

The polynucleotides encoding the immunogenic polypeptides described above may also have the coding sequence fused in frame to a marker sequence which allows for purification of the polypeptides of the present invention. The marker sequence may be, for example, a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention also relates to vectors which include polynucleotides encoding one or more of the polypeptides of the invention, host cells which are genetically engineered with vectors of the invention and the production of such immunogenic polypeptides by recombinant techniques in an isolated and substantially immunogenically pure form.

Host cells are genetically engineered (transduced or transformed or transfected) with the vectors comprising a polynucleotide encoding a polypeptide of the invention. The vector may be, for example, in the form of a plasmid, a viral particle, a phage, etc. The engineered host cells can be cultured in conventional nutrient media modified as appropriate for activating promoters, selecting transformants or amplifying the polynucleotides which encode such polypeptides. The culture conditions, such as temperature, pH and the like, are those previously used with the host cell selected for expression, and will be apparent to the ordinarily skilled artisan.

Vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the proteins.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial. pQE70, pQE60, pQE-9 (Qiagen, Inc.), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacl, lacZ, T3, T7, gpt, lambda $P_R$, $P_L$ and TRP. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterblogous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, a french press, mechanical disruption, or use of cell lysing agents, such methods are well know to those skilled in the art. However, preferred are host cells which secrete the polypeptide of the invention and permit recovery of the polypeptide from the culture media.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and/or purified from recombinant cell cultures by well-known protein recovery and purification methods. Such methodology may include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. In this respect, chaperones may be used in such a refolding procedure. Finally, high performance liquid chromatography (HPLC) can be employed for final purification steps.

The polypeptides that are useful as immunogens in the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated.

Procedures for the isolation of the individually expressed polypeptides may be isolated by recombinant expression/isolation methods that are well-known in the art. Typical examples for such isolation may utilize an antibody to a conserved area of the protein or to a His tag or cleavable leader or tail that is expressed as part of the protein structure.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole; et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The invention will be further described with respect to the following examples; however, the scope of the invention is not limited thereby:

EXAMPLE 1

Active Protection with Anti-Sp36

A. Cloning, expression, and purification of SP36

The genomic DNA used as target for amplification was isolated from *S. pneumoniae* Norway strain (serotype 4), the same strain used for genomic sequencing. The complete sequence of the Sp36 gene (SEQ ID NO:9), and its predicted amino acid sequence (SEQ ID NO:8), are given in the Sequence Listing appended hereto. It was noted that the predicted amino acid sequence included a hydrophobic leader sequence followed by a sequence (LSVC) similar to the consensus sequence for Type II signal peptidase (LxxC, in which both x's typically represent small amino acids). Primers (listed as SEQ ID NOS:1–3) were designed that would amplify the Sp36 gene and allow its cloning into pQE10 and expression as a histidine-tagged protein lacking the signal sequence for purification by nickel-affinity chromatography. Cloning of the fragment amplified by SEQ ID Nos 1 and 3 would result in a protein containing amino acids 21 through 819 of Sp36; cloning of the fragment amplified by SEQ ID Nos 2 and 3 would result in a protein containing amino acids 26 through 819 of Sp36 (amino acid numbers refer to SEQ ID NO:8).

B. Active Protection With Sp36 Vaccination

In each of the three experiments shown in FIGS. 1A–1C, C3H/HeJ mice (10/group) were immunized intraperitoneally (i.p.) with Sp36 protein (15 μg in 50 μl PBS emulsified in 50 μl complete Freund's adjuvant (CFA)). A group of 10 sham-immunized mice received PBS with adjuvant. A second immunization of 15 μg protein with incomplete Freund's adjuvant (IFA) was administered 4 weeks later; the sham group received PBS with IFA. Blood was drawn (retro-orbital bleed) at weeks 3, 6, and 9; and sera from each group were pooled for analysis of anti-Sp36 antibody by ELISA. Mice were challenged at week 10 by an i.p. injection of approximately 500 CFU *S. pneumoniae* strain SJ2 (serotype 6B; provided by P. Flynn, St. Jude Children's Research Hospital, Memphis, Tenn.). In preliminary experiments, the $LD_{50}$ of this strain was determined to be approximately 10 CFU. Mice were monitored for 14 days for survival.

The three experiments shown in FIGS. 1A–1C used slightly different preparations of recombinant Sp36. The experiments shown in FIG. 1A and 1B both used Sp36 containing amino acids 20–815, but different batches of protein were used in the two experiments. The experiment shown in FIG. 1C used Sp36 containing amino acids 25–815.

In the experiment shown in FIG. 1A, 9-week sera collected from the ten mice immunized with Sp36 (first batch) had an endpoint ELISA titer of 1:4,096,000. No anti-Sp36 antibody was detected in sera from sham-immunized mice. One hundred percent of the mice immunized with Sp36 protein survived the challenge (520 cfu of pneumococci) for 14 days. Eighty percent of sham-immunized mice were dead by day 4, and the remainder survived.

In the experiment shown in FIG. 1B, 9-week sera collected from the ten mice immunized with Sp36 (second batch) had an endpoint ELISA titer of >1:4,096,000. No anti-Sp36 antibody was detected in sera from sham-immunized mice. One hundred percent of the mice immunized with Sp36 protein survived the challenge (510 cfu of pneumococci) for 14 days. Of the sham-immunized mice; eighty percent were dead by day 4, and all died by day 9.

In the experiment shown in FIG. 1C, 9-week sera collected from the ten mice immunized with Sp36 (containing amino acids 25–815) had an endpoint ELISA titer of 1:4, 096,000. No anti-Sp36 antibody was detected in sera from sham-immunized mice. One hundred percent of the mice immunized with Sp36 protein survived the challenge (510 cfu of pneumococci) for 14 days. Of the sham-immunized mice, ninety percent died by day 4, and all died by day 12. These data demonstrate that immunization of mice with recombinant Sp36 proteins elicits a response capable of protecting against systemic pneumococcal infection and death. This protection was not strain-specific: the recombinant pneumococcal protein was cloned from a serotype 4 strain, while the challenge was with a heterologous strain, SJ2 (serotype 6B).

EXAMPLE 2

Passive Protection with Anti-Sp36 Antisera

A. Generation of Rabbit Immune Sera

Following collection of preimmune serum, a New Zealand White rabbit was immunized with 250 pg of Sp36 (containing amino acids 20–815) in CFA. The rabbit was given two boosts of 125 μg Sp36 in IFA on days 29 and 50 and bled on days 39 and 60. A second rabbit was immunized with a control antigen, *E. coli* FimC.

B. Passive Protection in Mice

Figure 2:
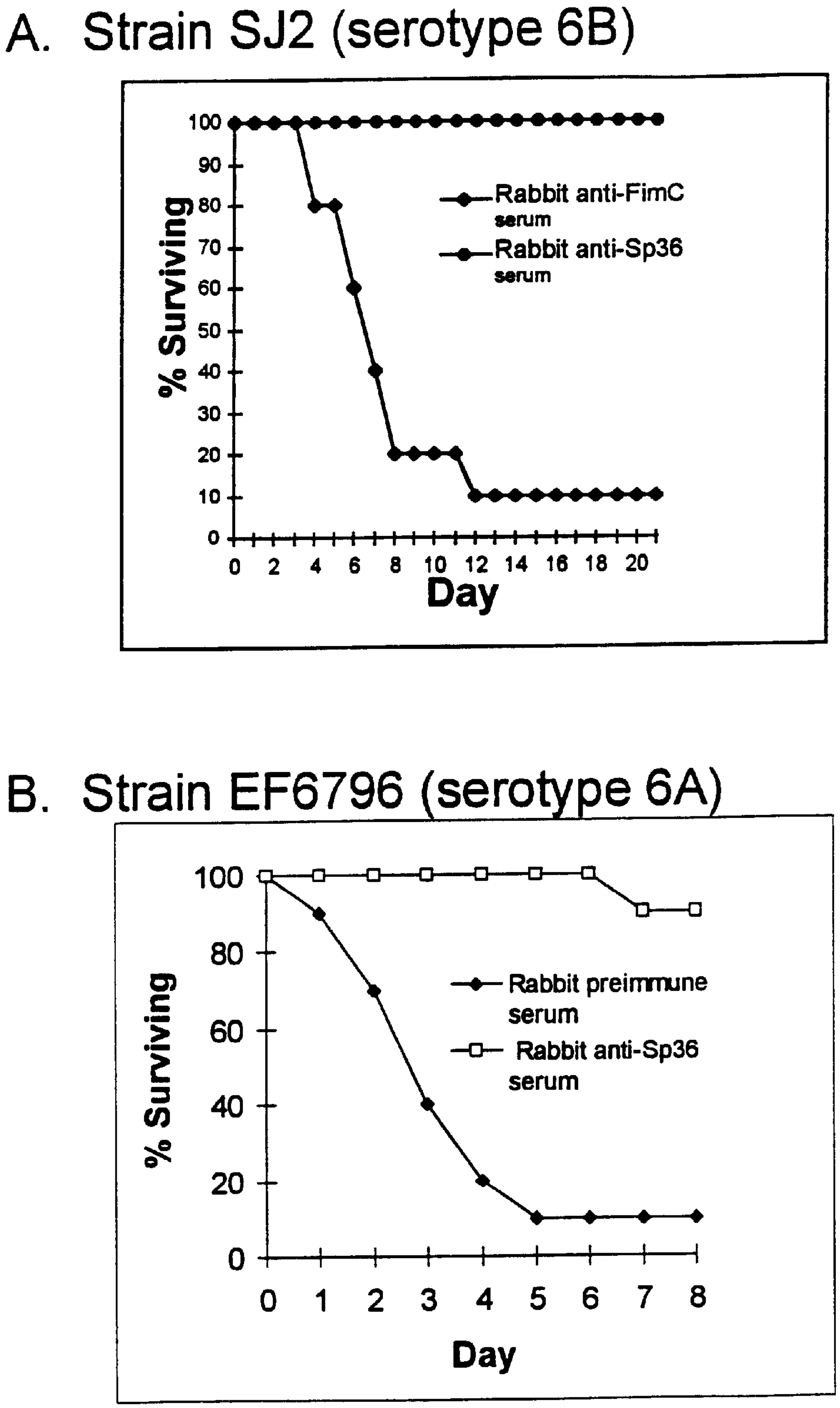
FIGS. 2A–2B show that passive administration of rabbit antiserum raised against Sp36 derived from Norway type 4 was able to protect mice in the pneumococcal sepsis model using two heterologous strains.

C3H/HeJ mice (10 mice/group) were passively immunized by two i.p. injections of 100 μl of rabbit serum. The first injection was administered twenty-four hours before challenge with 172 cfu of *S. pneumoniae* strain SJ2, and the second injection was given four hours after challenge. FIG. 2 shows the survival of mice after infection with two different strains of pneumococci.

FIG. 2A shows that of mice injected with 172 cfu of strain SJ2 (FIG. 2A), one hundred percent of the mice immunized with rabbit immune serum raised against Sp36 protein survived the 21-day observation period. Of the mice immunized with the control serum (anti-FimC), eighty percent died by day 8, and ninety percent died by day 12. FIG. 2B shows that of mice injected with 862 cfu of strain EF6796, ninety percent of the mice immunized with rabbit immune serum raised against Sp36 protein survived the 8-day observation period. Of those given a control serum (collected from a rabbit before immunization), ninety percent died by day 8.

These data indicate that the protection against pneumococcal infection resulting from immunization with Sp36 is antibody-mediated, since mice can be protected by passive transfer of serum from a hyperimmunized rabbit. As seen in the mouse active challenge experiments described above, serum directed against recombinant Sp36 protein cloned from a serotype 4 strain was protective against challenge with heterologous strains.

EXAMPLE 3

Conservation of Sp36 Among Strains of *S. pneumoniae*

A. Western Blotting

The 23 pneumococcal strains used in this experiment were obtained from the American Type Culture Collection (Rockville, Md.) and include one isolate each of the 23 serotypes in the multivalent pneumococcal vaccine. For total cell lysates, pneumococci were grown to mid-logarithmic phase (optical density at 620 nm, 0.4 to 0.6) in 2 ml Todd-Hewitt broth with 0.5% yeast extract (Difco, Detroit, Me.) at 37° C. Bacteria were harvested by centrifugation and washed twice with water. Pellets were resuspended in 200 μl lysis buffer (0.01% sodium dodecyl sulfate, 0.15 M sodium citrate and 0.1% sodium deoxycholate) and incubated at 37° C. for 30 min, then diluted in an equal volume 2×SSC (0.3 M sodium chloride, 0.03 M sodium citrate). Lysates were separated by SDS-PAGE, transferred to nitrocellulose membranes (Bio-Rad Laboratories, Hercules, Calif.), and probed with antibody in a standard Western blotting procedure. Sera from ten C3H/HeJ mice immunized with Sp36 (as described in Example 1) were pooled and used at a dilution of 1:3000. Bound antibody was detected with peroxidase-conjugated sheep anti-mouse IgG using the chemiluminescence kit from Amersham, Inc. (Cambridge, Mass.).

Figure 3:
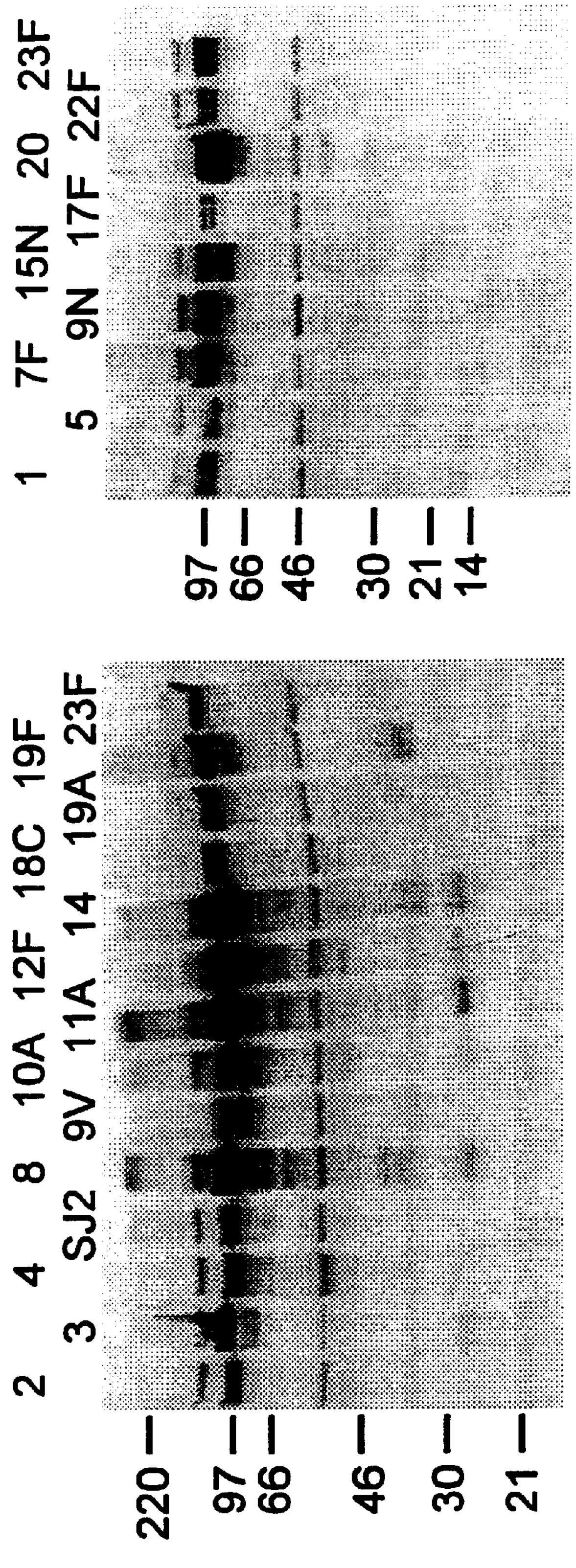
FIG. 3 is a western blot demonstrating the ability of antisera raised against recombinant Sp36 derived from strain Norway type 4 to react with Sp36 of heterologous strains. Total cell lysates were immunoblotted with mouse antisera to Sp36. A band representing Sp36 protein was detected in all 23 *S. pneumoniae* strains tested, which included isolates from each of the 23 pneumococcal serotypes represented in the current polysaccharide vaccine.

The mouse anti-Sp36 sera detected two major bands with apparent molecular weights of 97 and 100 kDa in all 23 pneumococcal lysates tested (shown in FIG. 3). The Sp36 signals obtained from *S. pneumoniae* serotypes 1, 5, 17F and 22F were lower, indicating either that the level of Sp36 expression is reduced in these strains, or that Sp36 in these strains is antigenically different.

These data show that Sp36 is antigenically conserved among strains of the 23 pneumococcal serotypes represented in the current polysaccharide vaccine.

B. Southern Blotting

Figure 4:
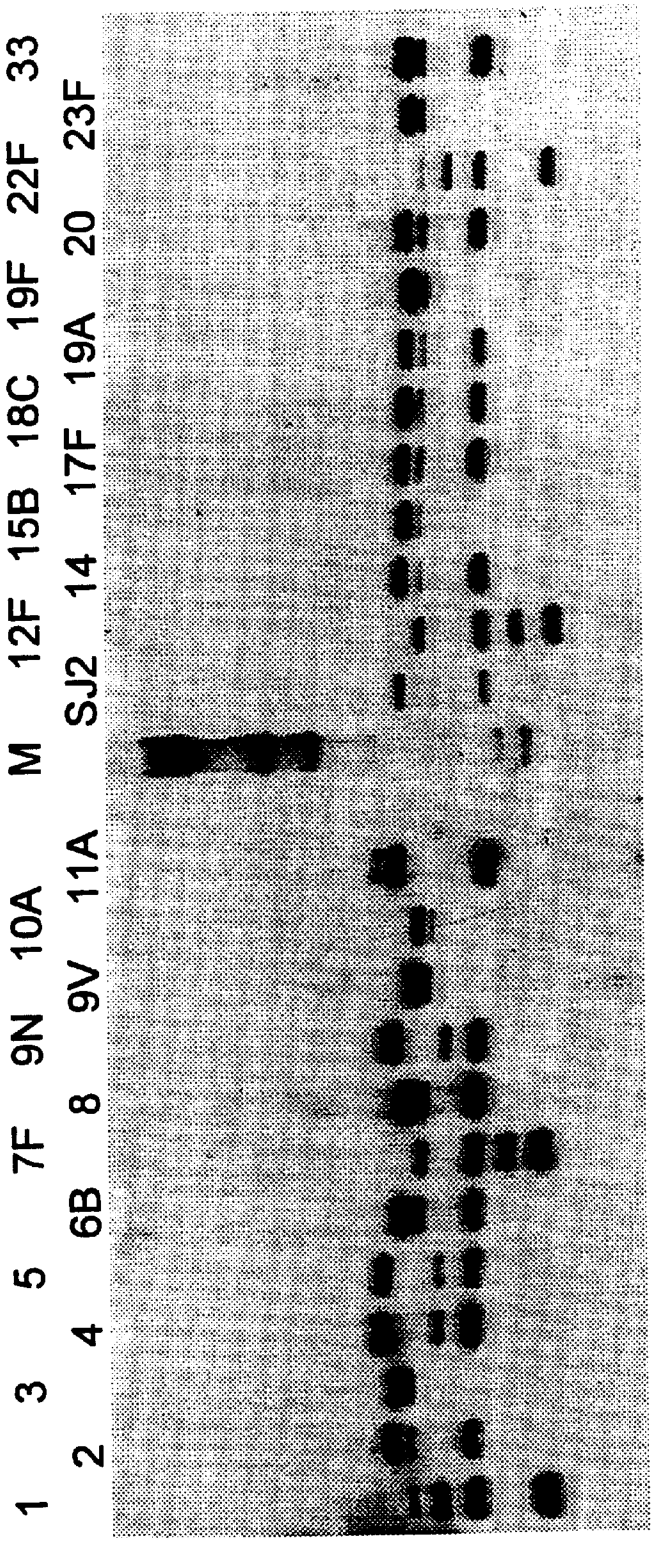
FIG. 4 is a Southern blot showing that the Sp36 gene from Norway type 4 hybridizes with genomic DNA from 24 other pneumococcal strains, indicating the presence of similar sequences in all these strains.

Genomic DNA was prepared from each of the 23 pneumococcal strains listed in the previous section and also from strain SJ2. DNA was digested with Pvull and BamHl, electrophoresed in an agarose gel and transferred to a nylon membrane. A probe was prepared by amplifying the Sp36 gene from Norway type 4 DNA (as in Example 1) and labeling the amplified fragment with fluorescein by the random-priming method, using a kit from Amersham. Hybridization, washing, and exposure of film were carried out as in the protocol supplied by Amersham. FIG. 4 shows that the Sp36 probe hybridized with DNA from each of the 24 strains studied. The lane marked "M" contained DNA from lambda phage, digested with HindIII and labeled with fluorescein, as molecular weight markers.

EXAMPLE 4

Immunogenicity of Sp36 in Humans

Figure 5:
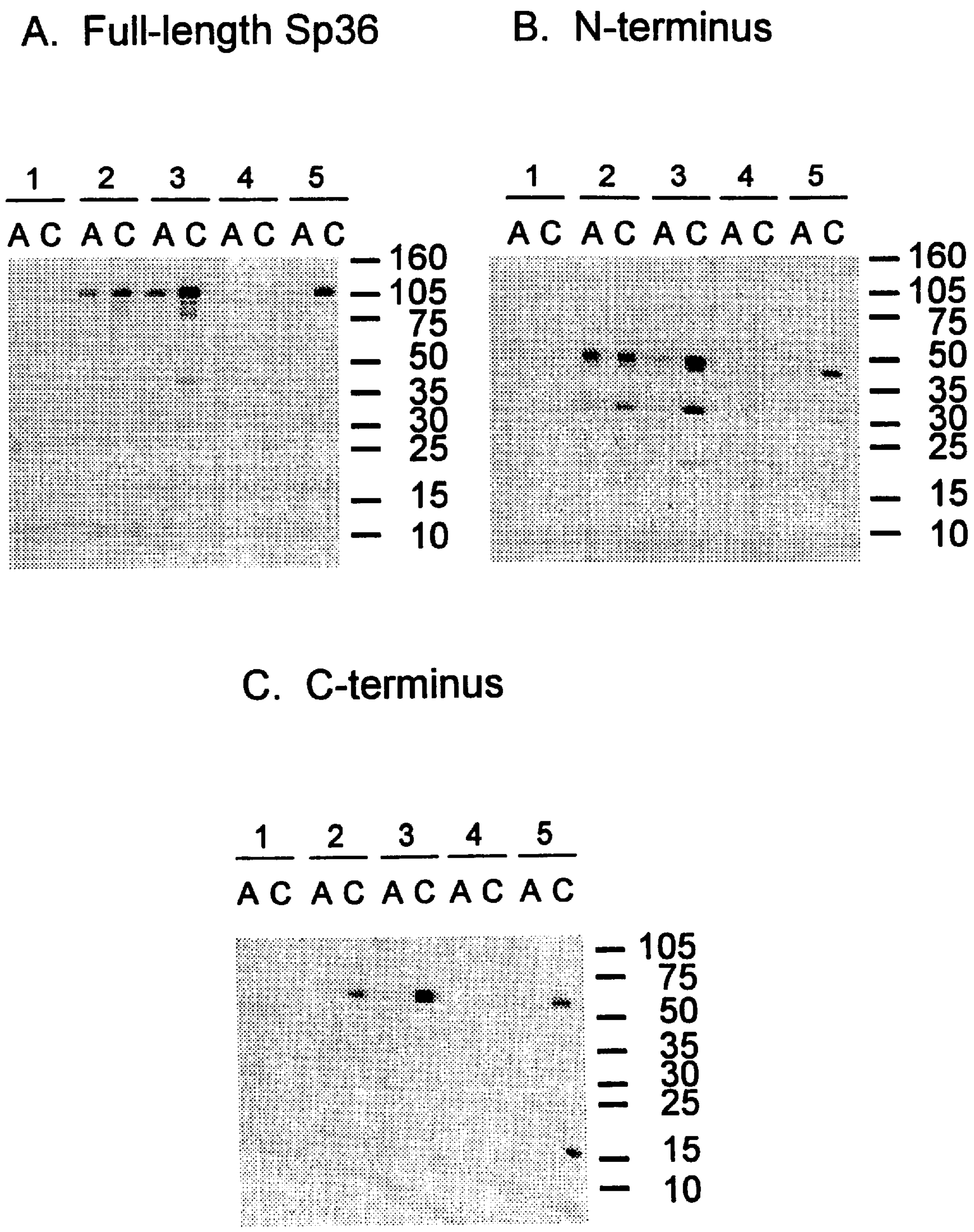
FIG. 5 is a western blot showing the reactivity of patient sera with Sp36. Sp36 (either full-length, panel A; N-terminal half, panel B; or C-terminal half, panel C) was electrophoresed by SDS-PAGE and transferred to nitrocellulose. Patient sera collected soon after the onset of illness (acute serum, lanes A) or eight to 30 days later (convalescent serum, lanes C) were used to probe the blots. For patients 2, 3, and 5, convalescent serum reacted more strongly with Sp36 than did the corresponding acute serum.

In order to determine whether Sp36 is immunogenic during human pneumococcal infection, sera from patients with culture-proven pneumococcal bacteremia were used in Western blots containing recombinant Sp36 protein. In the experiment shown in FIG. 5, sera from five patients (indicated as 1 through 5) were diluted 1:3000 and used to probe blots containing full-length Sp36, the N-terminal half of Sp36 (preceding the proline-rich region), or the C-terminal half of Sp36 (following the proline-rich region). Lanes labeled A (acute) were probed with serum collected shortly after diagnosis of pneumococcal infection; lanes C (convalescent) were probed with serum collected either one month later (patients 1, 2, and 3) or eight days after the first serum collection (patients 4 and 5). For patients 2, 3 and 5, reactivity of the convalescent serum with Sp36 was stronger that that of the corresponding acute serum. The difference between the acute and convalescent sera was particularly evident for reactivity with the C-terminal half of the protein.

In additional experiments (not shown), convalescent sera from 23 patients with pneumococcal infections were tested individually for reactivity with full-length Sp36: 20 of the 23 sera were found to bind Sp36 on a Western blot.

These experiments indicate that Sp36 is recognized by the human immune system and suggest that antibodies able to bind the Sp36 protein may be produced during natural *S. pneumoniae* infection in humans. Since the patients were infected with a variety of pneumococcal strains, these data also support the idea that Sp36 is antigenically conserved.

EXAMPLE 5

Table 1 Provides the Percent Identity Between the Various Sequences

Alignment of the predicted amino acid sequences of PhtA, PhtB, PhtD, and PhtE using the MEGALIGN program of Lasergene showed strong N-terminal homology with substantial divergence of the C-termini (FIG. 6). The alignment of the nucleotide sequences of the same genes is shown in FIG. 7. Amino acid and nucleotide sequences were compared using the identity weighting in a Lipman-Pearson pairwise alignment, in which the number of matching residues is divided by the total of matching residues plus the number of mismatched residues plus the number of residues in gaps. In the table below, the percent identity between each pair of sequences is shown at the intersection of the corresponding row and column.

EXAMPLE 6

Active Protection with PhtD Vaccination.

Mice immunized with recombinant PhtD derived from strain N4 generated potent antibody titers (reciprocal end-point titers ranging from 2,048,00 to 4,096,000). Mice immunized with PhtD were protected against death following intraperitoneal injection with either of three heterologous strains, SJ2 (serotype 6B; provided by P. Flynn, St; Jude Children's Research Hospital, Memphis, Tenn.), EF6796 (serotype 6A) or EF5668 (serotype4; both strains provided by D. Briles, University of Alabama, Birmingham). In the experiment shown in FIG. 8 (Panel A), all ten of the sham-immunized mice died within 10-days after challenge with virulent pneumococci (strain SJ2), while eighty percent of the PhtD-immunized mice survived the 15-day observation period. Immunization with PhtD also protected against a serotype 6A strain, EF6796 (Panel B) and a serotype 4 strain, EF5668 (Panel C). In the experiment shown in FIG. 8 (Panel B), all ten of the sham-immunized mice died within 7-days after challenge with virulent pneumococci (strain EF6796), while ninety percent of the PhtD-immunized mice survived the 15-day observation period. In the experiment shown in FIG. 8 (Panel C), all ten of the sham-immunized mice died within 6-days after challenge with virulent pneumoccoci (strain EF5668), while eight of nine mice immunized with PhtD survived the 15-day observation period.

TABLE 1

Percent Identities

| | PhtA | PhtB | PhtD | PhtE |
|---|---|---|---|---|
| | Percent Identity Between Amino Acid Sequences | | | |
| PhtA | — | 66.4 | 63.9 | 49.5 |
| PhtB | | — | 87.2 | 49.5 |
| PhtD | | | — | 49.8 |
| PhtE | | | | — |
| | Percent Identity Between Nucleotide Sequences | | | |
| PhtA | — | 58.3 | 59.3 | 47.9 |
| PhtB | | — | 86.4 | 47.4 |
| PhtD | | | — | 47.9 |
| PhtE | | | | — |

What is claimed is:

1. A composition comprising a polypeptide at least 95% identical to amino acids 20–838 of SEQ ID NO: 4 in a pharmaceutically accptable carrier in an amount effective to elicit production of an antibody that ends to *S. pneumoniae* when said composition is administered to a mammal.

2. The composition of claim 1 wherein said percent identity is at least 97%.

3. The composition of claim 1 wherein said polypeptide has the sequence of amino acids 20–838 of SEQ ID NO: 4.

4. A composition comprising an active fragment of a polypeptide at least 95% identical to amino acids 20–838 of SEQ ID NO: 4 wherein said active fragment comprises at least two coiled coil regions and is in a pharmaceutically acceptable carrier in an amount effective to elicit production of an antibody that binds to said polypeptide when said composition is administered to a mammal.

5. The composition of claim 4 wherein said active fragment further comprises at least 5 histidine triad regions.

6. A composition comprising a polypeptide comprising the sequence of amino acid residues 139–791 of SEQ ID NO: 4.

7. A vaccine comprising a polypeptide containing the sequence of amino acids 20–838 of SEQ ID NO: 4 in a pharmaceutically acceptable carrier in an amount effective to protect against pneumococcal infection when administered to a mammal.

8. A process for preventing infection caused by *S. pneumoniae* comprising administering the vaccine of claim 7.

9. An isolated polypeptide at least 95% identical to amino acids 20–838 of SEQ ID NO: 4, wherein said polypeptide binds to an antibody that binds *S. pneumoniae*.

10. The isolated polypeptide of claim 9 wherein said percent identity is at least 97%.

11. The isolated polypeptide of claim 9 wherein said isolated polypeptide has the sequence of amino acids 20–838 of SEQ ID NO: 4.

* * * * *

UNITED STATES PATENT AND TRADEMARK OFFICE

CERTIFICATE OF CORRECTION

PATENT NO. : 6,582,706 B1
APPLICATION NO. : 09/468656
DATED : June 24, 2003
INVENTOR(S) : Leslie S. Johnson et al.

It is certified that error appears in the above-identified patent and that said Letters Patent is hereby corrected as shown below:

In the Specification:

1. At column 3, line 30, delete "FIG. 6 is" and insert therefor --Figures 6A – 6F show--

2. At column 3, line 36, insert the statement --Figures 6A-6F follow in sequence and may collectively be considered as Figure 6--

3. At column 3, line 37, delete "FIG. 7 is" and insert therefor --Figures 7A – 7R show--

4. At column 3, line 42, insert the statement --Figures 7A-7R follow in sequence and may collectively be considered as Figure 7--

Figure 8A:
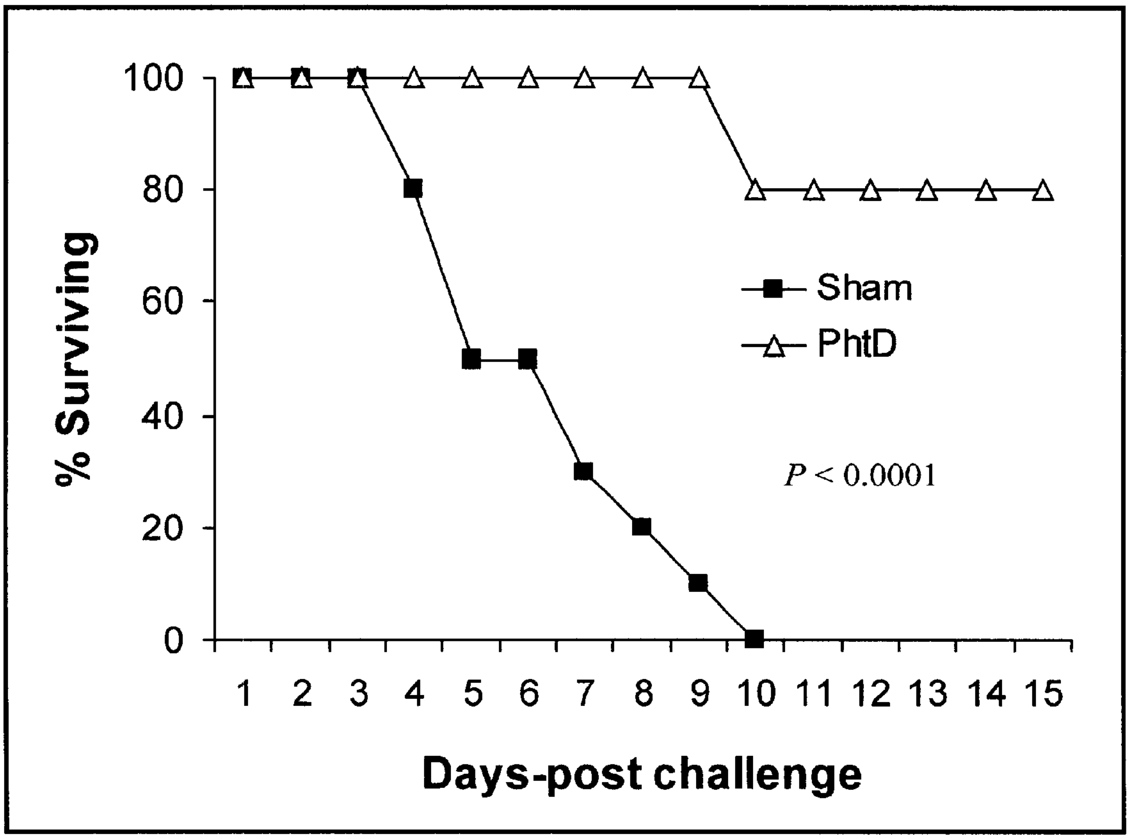
FIG. 8 shows the results of immunization of mice with PhtD recombinant protein, which leads to protection from lethal sepsis. C3H/HeJ (Panel A and B) or Balb/cByJ (Panel C) mice were immunized subcutaneously with PhtD protein (15 $\mu$g in 50 $\mu$l PBS emulsified in 50 $\mu$l complete Freund's adjuvant (CFA)). The recombinant PhtD protein used in protection experiments consisted of 819 amino acid residues, starting with the cysteine (residue 20). A group of 10 sham-immunized mice received PBS with adjuvant. A second immunization of 15 $\mu$g protein with incomplete Freund's adjuvant (IFA) was administered 3 weeks later; the sham group received PBS with IFA. Blood was drawn (retro-orbital bleed) at week 7; and sera from each group was pooled for analysis of anti-PhtD antibody by ELISA. Mice were challenged at week 8 by an intraperitonial (i.p.) injection of approximately 550 CFU *S. pneumoniae* strain SJ2, serotype 6B (Panel A), 850 CFU of strain EF6796, serotype 6A (Panel B) or 450 CFU of strain EF5668, serotype 4 (Panel C). In preliminary experiments, the $LD_{50}$ for strain SJ2 and EF6796 were determined to be approximately 10 CFU for both strains. The $LD_{50}$ for strain EF5668 was determined to be <5 CFU. Survival was determined in all groups over the course of 15 days following challenge. Data are presented as the percent survival for a total of 10 mice per experimental group. Two-sample Log-rank test was used for statistical analysis comparing recombinant Pht immunized mice to sham-immunized mice.
Figure 8B:
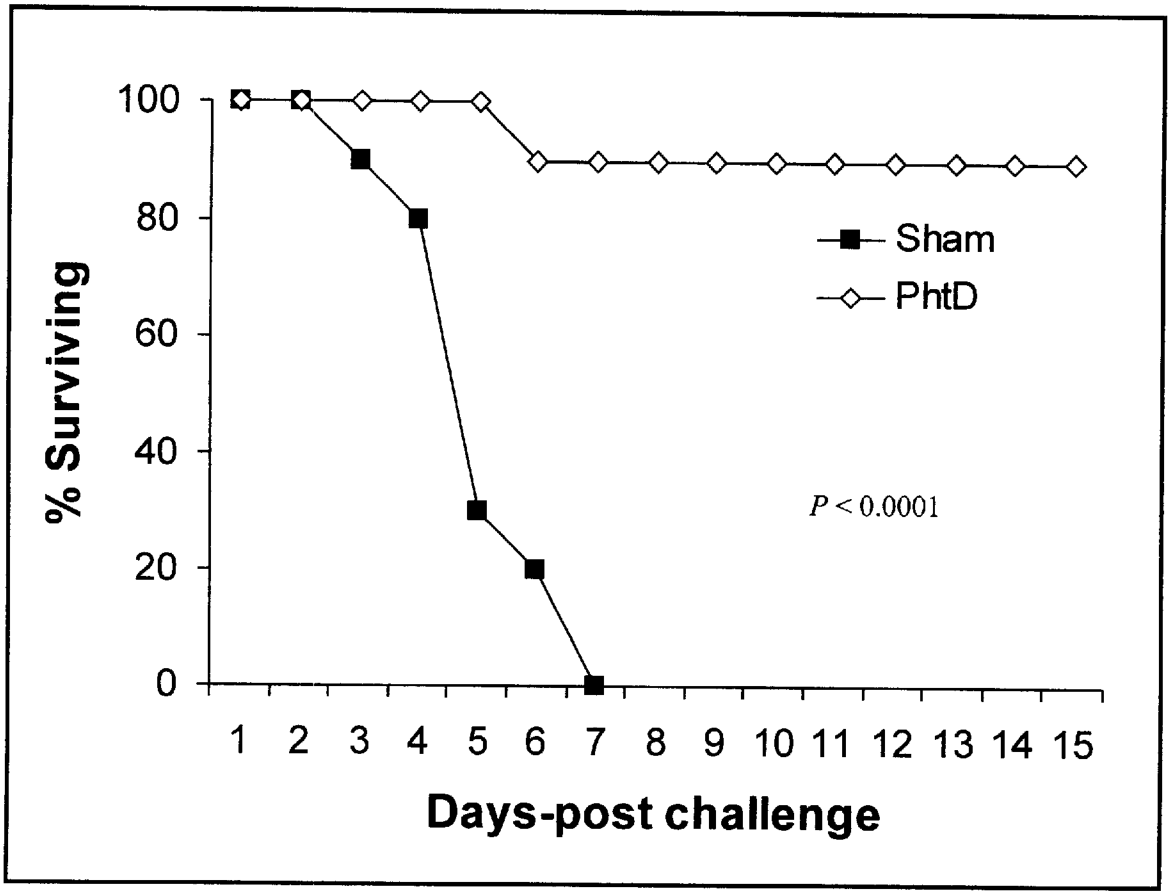
Figure 8C:
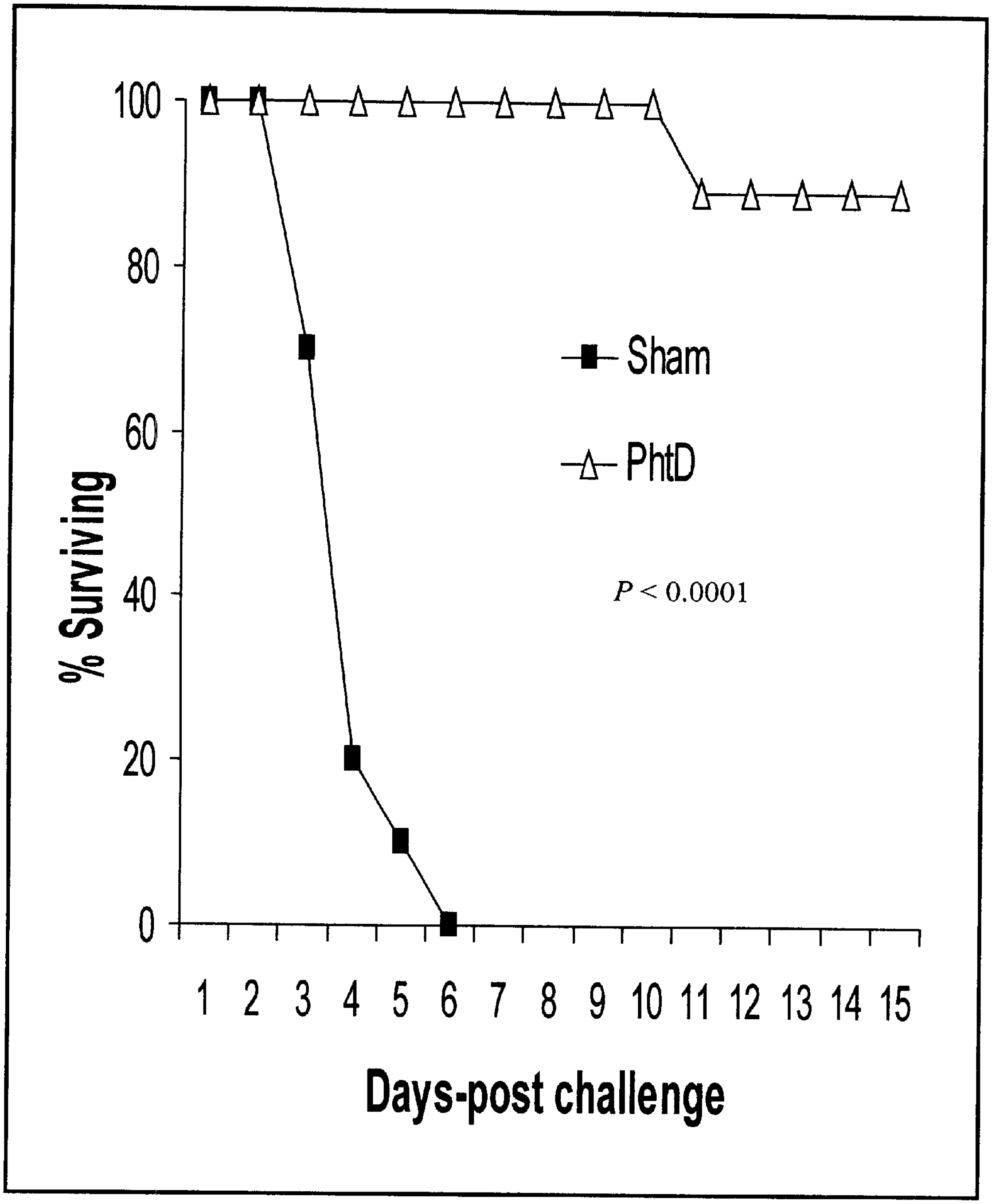

5. At column 3, line 43, delete "FIG. 8 is" and insert therefor --Figures 8A – 8C show--

6. At column 3, line 45, delete "Panel A and B" and insert therefor --Figures 8A and 8B--

7. At column 3, line 45, delete "Panel C" and insert therefor --Figure 8C--

8. At column 3, line 59, delete "Panel A" and insert therefor --Figure 8A--

9. At column 3, line 60, delete "Panel B" and insert therefor --Figure 8B--

10. At column 3, line 61, delete "Panel C" and insert therefor --Figure 8C--

11. At column 14, line 29, delete "serotype4" and insert therefor --serotype 4--

12. At column 14, line 31, delete "FIG. 8 (Panel A)" and insert therefor --Figure 8A--

UNITED STATES PATENT AND TRADEMARK OFFICE

CERTIFICATE OF CORRECTION

PATENT NO. : 6,582,706 B1
APPLICATION NO. : 09/468656
DATED : June 24, 2003
INVENTOR(S) : Leslie S. Johnson et al.

It is certified that error appears in the above-identified patent and that said Letters Patent is hereby corrected as shown below:

In the Specification:

13. At column 14, line 40, delete "FIG. 8 (Panel B)" and insert therefor --Figure 8B--

14. At column 14, line 45, delete "FIG. 8 (Panel C)" and insert therefor --Figure 8C--

15. At column 39, line 3 of claim 1, delete "accptable" and insert therefor --acceptable--

16. At column 42, line 7, delete "polypeptide" and insert therefor --protein--

Signed and Sealed this

Eighteenth Day of August, 2009

David J. Kappos
*Director of the United States Patent and Trademark Office*

UNITED STATES PATENT AND TRADEMARK OFFICE

CERTIFICATE OF CORRECTION

PATENT NO. : 6,582,706 B1 Page 1 of 1
APPLICATION NO. : 09/468656
DATED : June 24, 2003
INVENTOR(S) : Leslie S. Johnson It is certified that error appears in the above-identified patent and that said Letters Patent is hereby corrected as shown below:

In the Claims:

At column 40, line 64 in Claim 1, delete "ends" and insert --binds--

Signed and Sealed this

Thirteenth Day of October, 2009

David J. Kappos
*Director of the United States Patent and Trademark Office*